United States Patent
Pfaller et al.

(10) Patent No.: US 6,551,797 B1
(45) Date of Patent: Apr. 22, 2003

(54) EXPRESSION SYSTEM FOR PRODUCING PROTEINS

(75) Inventors: Rupert Pfaller, München (DE); Johanna Hessing, Delft (NL); Cornelis van den Hondel, Gouda (NL); Robertus van Gorcom, Soest (NL)

(73) Assignee: Consortium für Electrochemische Industrie GmbH, München (DE)

( * ) Notice: Subject to any disclaimer, the term of this patent is extended or adjusted under 35 U.S.C. 154(b) by 0 days.

(21) Appl. No.: 09/647,492

(22) PCT Filed: Apr. 1, 1999

(86) PCT No.: PCT/EP99/02252

§ 371 (c)(1),
(2), (4) Date: Feb. 28, 2001

(87) PCT Pub. No.: WO99/51757

PCT Pub. Date: Oct. 14, 1999

(30) Foreign Application Priority Data

Apr. 2, 1998 (DE) .......................................... 198 14 853

(51) Int. Cl.$^7$ .......................... C12P 21/06; C12N 15/63; C12N 15/85; C12N 15/87; C12N 15/09
(52) U.S. Cl. ................... 435/69.1; 435/455; 435/320.1; 536/23.1
(58) Field of Search ...................... 536/23.1; 435/320.1, 435/455, 69.1

(56) References Cited

U.S. PATENT DOCUMENTS 6,008,029 A * 12/1999 Yaver et al. ................ 435/189

FOREIGN PATENT DOCUMENTS

| JP | 09047289 | 2/1997 |
|----|----------|--------|
| WO | 9312259  | 6/1993 |
| WO | 9600290  | 1/1996 |

* cited by examiner

*Primary Examiner*—Remy Yucel
*Assistant Examiner*—Tina Katcheves
(74) *Attorney, Agent, or Firm*—Collard & Roe, P.C.

(57) ABSTRACT

An expression system for producing a protein in a filamentous fungus, consisting of a) a host organism selected from the species Trametes and Polyporus and b) a DNS vector containing a selection marker gene. This selection marker gene code is a protein which allows the selection of positive transformants after the transformation of the host organism and which is selected from the group of: antibiotics-resistant genes coding for proteins which eliminate the growth-inhibitory effect of antibiotics against which the host organism is not resistant. Genes coding proteins which are capable of a color-causing reaction; and genes complementing a genetic defect of the host organism (auxotrophy), the expression of the selection marker gene is controlled by at least one active genetic regulation element in the host organism, and c) a DNS vector containing a gene which codes the protein to be produced. The expression of this gene and optionally, the secretion of the protein so produced are controlled by an active genetic regulation element in the host organism. The DNS vector containing a section marker gene and the DNS vector containing the gene which codes the protein to be produced can also be in the form of one DNS vector.

11 Claims, 4 Drawing Sheets

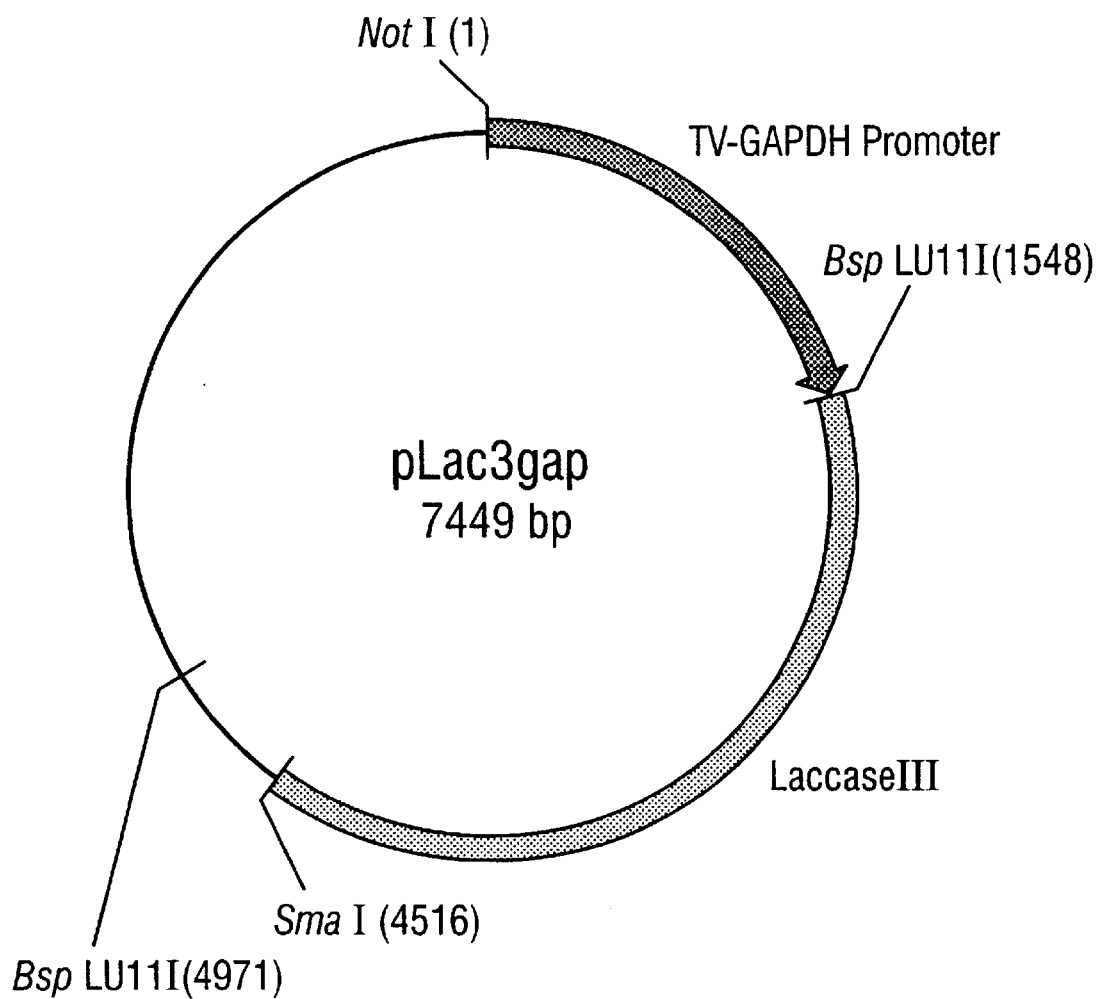

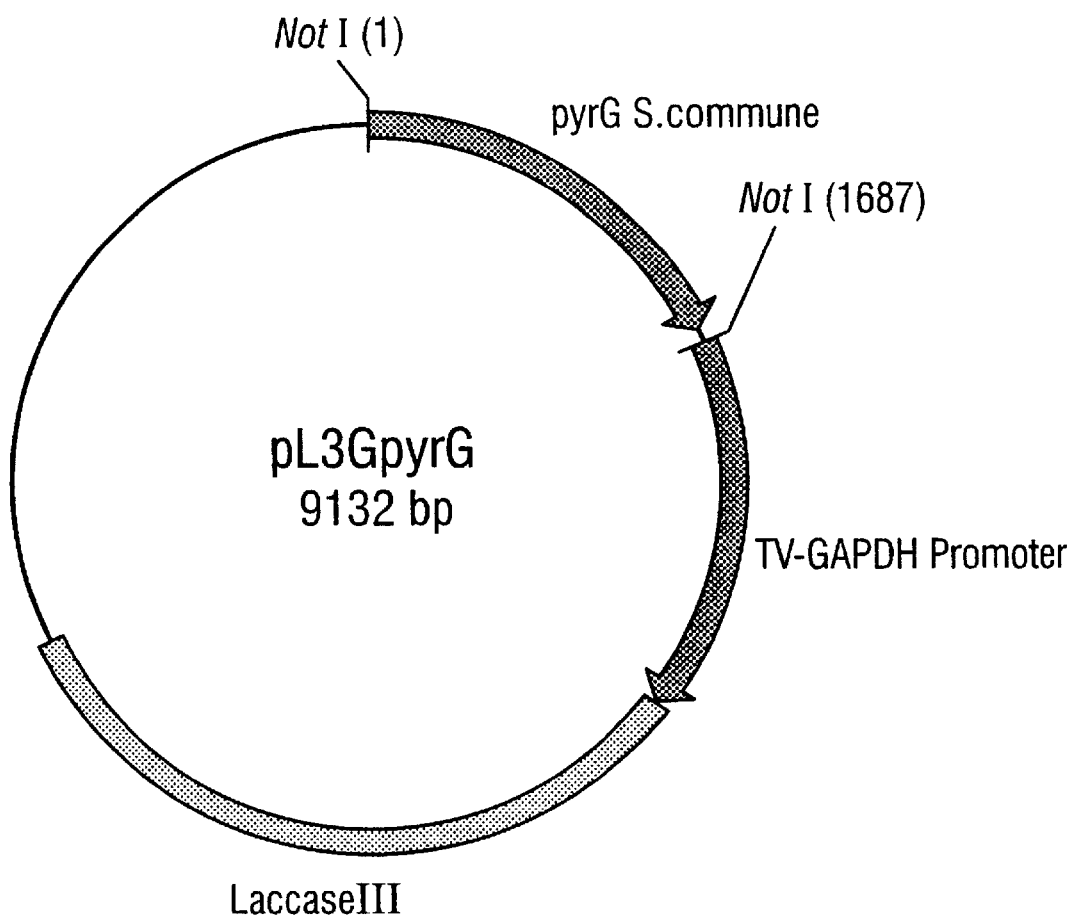

Primer A: 5'-TCCAGCTCGACCTTGCGCCGC-3'        SEQ ID NO: 4
Primer B: 5'-GGATCCGACGTGGAGGAGCCG-3'        SEQ ID NO: 5

Primer C: 5'-TGGCAYGGNTTYTTYCA-3'            SEQ ID NO: 6
Primer D: 5'-TCDATRTGRCARTG-3'               SEQ ID NO: 7
Primer E: 5'-ATTCAG<u>GGATCC</u>TGGTAYCAYWSNCAY-3'   SEQ ID NO: 8
Primer F: 5'-ATACGA<u>GGATCC</u>RTGNCCRTGNARRTG-3'   SEQ ID NO: 9

Primer G: 5'-CGTATCGGCCGTATCGTCCTCCG-3'     (SEQ ID NO: 10)
Primer H: 5'-CGCCCTTCAAGTGGGCAGAGGCC-3'     (SEQ ID NO: 11)

5'- AATTCGCGGCCGC-     -3'    SEQ ID NO: 12
3'-     GCGCCGGCGTTAA -5'    SEQ ID NO: 13

EXPRESSION SYSTEM FOR PRODUCING PROTEINS

BACKGROUND OF THE INVENTION

1. Field of the Invention

The invention relates to an expression system for production of proteins in fungi of the genera Trametes or Polyporus, to its preparation and to its use.

2. The Prior Art

Various prokaryotic and eukaryotic expression systems are known for protein production. Examples of prokaryotic expression systems are *Escherichia coli* and *Bacillus subtilis*. The methods for genetic manipulation of these organisms are well established. Specific disadvantages of these expression systems are the frequently disappointingly low production rate in particular of eukaryotic proteins, the folding of the produced proteins in such a way that they are often not in active form, and, in particular, the absence of the post-translational modification of the expressed proteins. As example of the absence of post-translational modification, mention may be made of the absence of incorporation of prosthetic groups or the absence of glycosylation of the protein to be expressed.

These disadvantages of prokaryotic expression systems can be avoided by using eukaryotic systems.

Widespread eukaryotic expression systems which are widely used include cell culture systems both of mammalian cells and insect cells, and eukaryotic microorganisms such as yeasts or filamentous fungi. Whereas the protein to be expressed is usually produced in active form with these expression systems, the production rate is in many cases too low, especially on expression of heterologous proteins. Expression in the yeast *Saccharomyces cerevisiae* or in filamentous fungi from the ascomycetes class may serve as example thereof.

High production rates in filamentous fungi such as Aspergillus have been described in particular for the expression of homologous proteins or proteins of filamentous fungi of the ascomycetes class. Expression of heterologous proteins often takes place with only low or moderate yields. WO 96/00290, for example, describes heterologous expression of the laccase LCC1 from the filamentous fungus of the basidiomycetes class, *Polyporus pinsitus*. On expression in Aspergillus, a filamentous fungus of the ascomycetes class, yields of up to 0.35 g/l are obtained in the fermentation. This is a comparatively small increase in yield compared with the production of 0.1–0.2 g/l by a comparable wild-type strain in the fermentation.

There is an increasing interest in industrial applications especially for enzymes from the basidiomycetes class and therein especially the white rot fungi. Examples which may be mentioned are hydrolytic enzymes such as cellulases, hemicellulases or lipases, or else oxidoreductases such as lignin peroxidases, manganese peroxidases, laccases, cellobiose-quinone oxidoreductase or cellobiose oxidase. Potential applications for these enzymes exist, for example, in wood and pulp processing.

One class of enzymes occurring among others in basidiomycetes and of great interest for industrial applications is the class of laccase enzymes (p-hydroxyphenol oxidase, EC 1.10.3.2.). Laccases belong to the protein family called the "blue copper proteins" and usually contain four copper ions which are arranged in three copper centers referred to as type 1 to type 3. Laccases are further distinguished by generally being secreted proteins and possibly containing a glycosylation content of up to 10 to 45% of the molecular weight. Beside the depolymerization of macromolecular compounds such as lignin, laccases are also able to catalyze the polymerization in particular of aromatic compounds. An example thereof is lignin biosynthesis in plants, in which the laccases present in plants are involved. Possible industrial applications of laccases are in paper manufacture for the delignification of pulp, in polymerization reactions of all types, for example in waste water treatment. The use of laccases in organic chemical synthesis is also known, for example in coupling reactions or the side-chain oxidation of aromatic compounds. However, a precondition for industrial application of all these processes is that the laccase enzyme can be provided at reasonable cost and in relatively large amounts.

DNA vectors said to be suitable for transformation and selection of transformants have been described for various filamentous fungi from the basidiomycetes class. A method for homologous transformation of the basidiomycete *Phanerochaete chrysosporium* has been described (M. Alic et al. (1991) Curr. Genet. 19, 491–494). DNA constructs for transformation of the basidiomycete *Pleurotus ostreatus* has been described (K. Yanai et al. (1996) Biosci. Biotech. Biochem. 60, 472–475). U.S. Pat No. 5,362,640 describes DNA vectors for the transformation of the basidiomycete *Coriolus hirsutus*. Likewise, a DNA vector for transformation of the basidiomycete *Coriolus versicolor* has been described (Y. Iimura et al. (1992) 5th International Conference on Biotechnology in the Pulp and Paper Industry, 427–431). It has not been disclosed for any of these expression systems from the basidiomycetes class that a significant increase in the expression rate for homologous or heterologous proteins has been achieved.

Known expression vectors containing genetic regulatory elements for expression in filamentous fungi of the ascomycetes class cannot be efficiently expressed in filamentous fungi of the basidiomycetes class. Thus, on transformation of filamentous fungi of the basidiomycetes class they do not allow the selection of positive transformants on the basis of, for example, acquired antibiotic resistance or the expression of a color-forming indicator protein or on the basis of the complementation of an auxotrophic gene defect.

SUMMARY OF THE INVENTION

The present invention relates to an expression system for the production of a protein in a filamentous fungi consisting of a) a host organism selected from the genera Trametes and Polyporus and b) a DNA vector which comprises a selection marker gene which codes for a protein which, after transformation of the host organism, allows selection of positive transformants and is selected from the group of antibiotic resistance genes which code for proteins which abolish the growth-inhibiting effect of antibiotics to which the host organism is not resistant, of genes which encode proteins which are capable of a color-forming reaction, and of genes which complement a genetic defect in the host organism (auxotrophy), where expression of the selection marker gene is controlled by at least one genetic regulatory element which is active in the host organism, and c) a DNA vector which comprises a gene which codes for the protein to be produced, where expression of this gene and, where appropriate, also secretion of the protein thus produced is controlled by a genetic regulatory element which is active in the host organism, where the DNA vector which comprises a selection marker gene, and the DNA vector which comprises the gene which codes for the protein to be produced may also be present as a DNA vector.

Suitable and preferred as antibiotic resistance genes are genes which confer resistance to an antibiotic from the group of hygromycin, bialaphos, kanamycin, geneticin, bleomycin, oligomycin, G418, zeocin, benomyl and phleomycin.

It is possible and preferred to use further selection marker genes which code for proteins which are capable of a color-forming reaction, for example the glucuronidase gene or the gene for green fluorescent protein (GFP).

Selection marker genes able to complement a genetic defect in the host organism (auxotrophy) are particularly suitable.

Host organisms preferred for the expression system according to the invention are monokaryotic strains from the genera Trametes and Polyporus.

Host organisms of the species *Trametes versicolor* are particularly preferred.

The host organism in the expression system according to the invention is preferably distinguished by also having a genetic defect in metabolism (auxotrophy), on the basis of which one or more metabolites essential for growth can no longer be synthesized, and the host organism is no longer able to grow on minimal media without addition of this or these metabolites.

The invention therefore also relates to an expression system wherein the host organism selected from the genera Trametes and Polyporus has a genetic defect in metabolism (auxotrophy) on the basis of which one or more metabolites essential for growth can no longer be synthesized, and the host organism is no longer able to grow on minimal media without addition of this or these metabolites, and the selection marker gene is selected in such a way that it complements the auxotrophic gene defect of the host organism.

Examples of selection marker genes able to complement an auxotrophic gene defect in the host organism are the OCT gene (codes for ornithine carbamoyltransferase, U.S. Pat. No. 5,362,640), the pyr G gene (codes for orotidine-5'-phosphate decarboxylase, Goosen et al., Curr. Genet. (1987) 11, 499–503), the trpC gene (codes for a trifunctional gene product which has enzymic activity for phosphoribosylanthranilate isomerase, glutamine amido-transferase and indolglycerol-phosphate synthase, Yelton et al., Proc Natl. Acad. Sci. USA (1984) 81, 1470–1474), or the nia D gene (codes for nitrate reductase).

The particularly preferred selection marker gene is the pyr G gene which codes for orotidine-5'-phosphate decarboxylase (an enzyme of uridine metabolism) and which is able to complement the uridine auxotrophy of a host strain deficient in the pyrG gene. The host organism which is particularly preferred in this case is a strain from the genus Trametes or Polyporus having a defect in the pyr G gene and auxotrophic for uridine.

The pyr G gene is preferably derived from a fungus from the basidiomycetes class, for example from the genus Agaricus, Coriolus, Polyporus, Pleurotus, Phanerochaete, Schizophyllum or Trametes.

Suitable and preferred for expression of the pyr G gene are the promoter and terminator elements for a glyceraldehyde-3-phosphate dehydrogenase gene (GAPDH gene), for example from the filamentous fungi from the basidiomycetes class *Schizophyllum commune*, *Agaricus bisporus* (the GAPDH Ag2 gene), *Phanerochaete chrysosporium*, *Trametes versicolor* or for a laccase gene, preferably the laccase I gene, or the laccase III gene from *Trametes versicolor*.

Particularly suitable as selection marker gene for the expression system according to the invention are the orotidine-5'-phosphate decarboxylase gene (pyr G gene), preferably from the basidiomycete *Schizophyllum commune* or from the basidiomycete *Trametes versicolor*.

Expression of the pyr G gene from the basidiomycete *Schizophyllum commune* is preferably controlled by the promoter and, where appropriate, terminator of the pyr G gene from *Schizophyllum commune*.

Expression of the pyr G gene from the basidiomycete *Trametes versicolor* is preferably controlled by the promoter of the pyr G gene from *Trametes versicolor*.

The expression system according to the invention is particularly suitable for expressing a gene which codes for a hydrolytic enzyme, for example from the group of cellulases, hemicellulases and lipases, or from the group of oxidoreductases such as, for example, the lignin peroxidases, manganese peroxidases, laccases, cellobiose-quinone oxidoreductase or cellobiose oxidase.

It is particularly preferably suitable for expression of a gene for a laccase.

The invention further relates to a DNA vector which comprises at least one selection marker gene which codes for a protein which, after transformation of a fungus selected from the genera Trametes and Polyporus, allows selection of positive transformants, wherein the selection marker gene is selected from the group of antibiotic resistance genes which code for proteins which abolish the growth-inhibiting effect of antibiotics to which the host organism is not resistant, of genes which encode proteins which are capable of a color-forming reaction, and of genes which complement a genetic defect in the host organism (auxotrophy), and wherein the selection marker gene is controlled by at least one genetic regulatory element active in the host organism.

The DNA vectors according to the invention allow the selection of positive transformants on the basis of complementation of an auxotrophic gene defect in the host organism on transformation of fungi selected from the genera Trametes and Polyporus.

In particular, the selection of transformants of the filamentous fungus *Trametes versicolor* and, in a particularly preferred embodiment, transformants of pyr G-deficient auxotrophic strains of *Trametes versicolor* is made possible by the genes mentioned as particularly preferred for complementation of auxotrophic gene defects in the host organism.

The DNA vectors according to the invention are also suitable for expression of genes which code for proteins in a host organism of the genus Trametes and Polyporus. Genes which code for proteins mean for the purpose of the invention also the cDNA genes derived from the structural genes for the proteins. The proteins may be proteins which are heterologous for the host organism or proteins which are homologous for the host organism.

The DNA vector according to the invention thus preferably also comprises at least one gene which codes for a protein to be expressed.

The DNA vector according to the invention particularly preferably comprises at least one gene which codes for a hydrolyzing enzyme, for example from the group of cellulases, hemicellulases and lipases, or from the group of oxidoreductases such as, for example, lignin peroxidases, manganese peroxidases, laccases, cellobiose-quinone oxidoreductase or cellobiose oxidase.

The DNA vector according to the invention particularly preferably comprises a gene for a laccase.

A promoter which is necessary for expression of the protein-encoding gene may originate from the gene to be expressed, or it is also possible to use the promoter of a foreign gene functionally linked to the coding region of the gene to be expressed.

The DNA vector according to the invention thus preferably also comprises a promoter for expression of the protein-encoding gene.

The DNA vector according to the invention particularly preferably comprises as promoter for expression of the protein-encoding gene a promoter which ensures a high level of expression.

A promoter preferably used for this purpose is, for example, the promoter of the gene for the protein glyceraldehyde-3-phosphate dehydrogenase (GAPDH) for example from the species *Trametes versicolor*.

The DNA vector according to the invention preferably also comprises a transcription terminator for the protein-encoding gene.

It is possible to use as transcription terminator the terminator of the protein-encoding gene to be expressed or else the terminator of a foreign gene. The transcription terminator of the gene of a laccase is preferred.

Expression of the proteins can take place intracellularly or, in the presence of a signal sequence capable of functioning for the purpose of secretion, also extra-cellularly.

If secretion of the expressed protein from the cell is desired, the DNA vector according to the invention preferably comprises a signal sequence capable of functioning 5' upstream of the protein-encoding gene. It is additionally possible for a so-called secretion carrier, functionally linked to the 5' end of the protein-encoding gene, to be present in the DNA vector according to the invention.

The secretion carrier can be the gene for a secreted protein or the fragment of a gene for a secreted protein. The secretion carrier can be functionally linked to the protein to be secreted in such a way that a fusion protein is produced from the secretion carrier and the protein to be secreted. In another embodiment, the linkage of secretion carrier and the protein to be secreted is designed so that the secretion carrier can be separated from the protein to be secreted. This can be brought about, for example, by inserting a recognition sequence for a protein-cleaving enzyme into the linkage site between secretion carrier and the protein to be secreted. An example of this which may be mentioned is the lysine-arginine recognition sequence for the so-called KEX2 protease and an example of a secretion carrier is the glucoamylase from *Aspergillus niger* (Contreras et al., Bio/Technology (1991) 9, 378–381, Broekhuijsen et al., J. of Biotechnology (1993) 31, 135–145).

DNA sequences which are involved other than as transcription terminators at the 3' end of the protein-encoding gene in the expression and secretion of the expressed protein can likewise be present in the DNA vector according to the invention. One example thereof is provided by the gene for the laccase from *Neurospora crassa*, whose 3' end contains the sequence for 13 amino acids which are deleted during secretion of the protein and are no longer present in the mature protein (Germann et al., J. Biol. Chem. (1988) 263, 885–896).

Preparation of the DNA vectors according to the invention takes place by methods known in the prior art. Various possibilities are explained in the examples. The methods described therein can be applied by the skilled worker to any desired other vectors, resistance genes, regulatory elements and structural genes.

The DNA vectors according to the invention are suitable for producing fungal strains which are capable of efficient expression and secretion of proteins.

The invention therefore also relates to processes for the production of fungal strains which are capable of the efficient expression and secretion of proteins.

This process comprises using as host organism a fungus selected from the genera Trametes and Polyporus which has an auxotrophic gene defect and which is transformed by methods known per se with a DNA vector which has a gene for complementation of the auxotrophic gene defect in the host strain, and selecting from the transformation mixture the clones transformed with the DNA vector by selection for complementation of the auxotrophic gene defect, where expression of the gene for complementation of the auxotrophic gene defect in the host strain is controlled by a genetic regulatory element which is active in the host strain.

Filamentous fungi which can be used as host for the gene expression belong to the genus Trametes or Polyporus.

The preferred host for the gene expression is a monokaryotic basidiomycete from the genus Trametes or Polyporus.

It is a further advantage for said host strains from the basidiomycetes class to have an auxotrophic gene defect which can be used as selection marker for identifying positive transformants. It is possible to use, for example, host strains from the basidiomycetes class which have a gene defect in the OCT gene, in the pyr G gene, in the trpC gene or in the nia D gene.

The preferred host for gene expression is a fungus selected from the genera Trametes and Polyporus and having a defect in the pyr G gene.

Particularly preferred for gene expression is a host of the species *Trametes versicolor* which has a defect in the pyr G gene and is auxotrophic for uridine.

Transformation of the host strain takes place by methods corresponding to the prior art. These methods include transformation of protoplasts by the $CaCl_2$/PEG method, transformation by electroporation or biolitic transformation by bombardment with DNA-containing microprojectiles. These methods are described in standard textbooks.

For example, the gene to be transformed is cloned in a known manner into a DNA vector according to the invention and introduced by the methods mentioned into a filamentous fungus selected from the genera Trametes and Polyporus.

However, the gene to be transformed can also be cloned into an expression vector without selection marker gene and used together with a vector which complements the auxotrophic gene defect in the host strain for generating transformants (cotransformation).

The preferred strain for the transformation is a filamentous fungus selected from the genera Trametes and Polyporus. The relevant strain from the basidiomycetes class can moreover be a monokaryotic or else a dikaryotic strain. In a preferred embodiment, it is a uridine-auxotrophic strain which has a defect in the pyr G gene.

Particularly preferred for the transformation is a monokaryotic, uridine-auxotrophic, pyr G-deficient strain from the species *Trametes versicolor*.

The selection of positive transformants takes place, for example, by placing protoplasts, after transformation with vector DNA, on a medium to which is added, for osmotic stabilization of the protoplasts, an addition such as, for example, sorbitol, mannitol or sucrose and which allows the selection of transformants with the complementing pyr G gene.

In a preferred embodiment of the invention, the filamentous fungus *Trametes versicolor* is transformed in a homologous system with the gene of a laccase from *Trametes versicolor*. This achieves an increase in the expression rate for said laccase, which significantly improves the production rate of 0.1 g of laccase/l of culture medium in the fermentation which can be achieved in the prior art.

Preferably used for this purpose is the promoter which is intrinsic to the laccase gene or the promoter for a strongly expressed gene from *Trametes versicolor*. The promoters of the laccase genes I and III, whose isolation is described in the 4th example, are preferably used. This entails using from the laccase I gene preferably the sequence section from base 1–1192 contained in SEQ ID NO: 1. The sequence section from base 1–547 of the laccase III gene contained in SEQ ID NO: 2 is preferably used. The promoter of another strongly expressed gene is represented by the GAPDH promoter for the glyceraldehyde-3-phosphate dehydrogenase from *Trametes versicolor*. Isolation of the GAPDH promoter is described in the 5th example. The GAPDH promoter sequence corresponds to the sequence section listed in SEQ ID NO: 3, base 1–1542. It has emerged that, in particular, the sequence section in SEQ ID NO: 3, base 1365 to bp 1542, and sequences homologous thereto and having a homology of greater than 73% are suitable for the expression. It is further preferred for at least one of the following sequence sections likewise to be present on the regulatory element according to the invention:

SEQ ID NO: 3: base 1005 to bp 1123, and sequences homologous to this sequence section and having a homology of greater than 52%; or SEQ ID NO: 3: base 817 to bp 947, and sequences homologous to this sequence section and having a homology of greater than 44%, or SEQ ID NO: 3: base 640 to bp 728, and sequences homologous to this sequence section and having a homology of greater than 50%.

All homology levels mentioned in the present invention relate to results obtained with the computer program "Wisconsin Package Version 9.1, Genetics Computer Group (GCG), Madison, Wis.". The homology determination takes place by searching the database with the subprogram "fasta" and the preset values (word size 6). The most similar sequences are then examined for homology with the subprogram "gap". The preset parameters "gap creation penalty 50". and "gap extension penalty 3" are used for this. In addition, the subprogram "gap" and the above-mentioned preset parameters were used to examine for homology the promoter sequence, which is disclosed in JP 09047289 but which is not yet available in a database, of the GAPDH gene from *Coriolus hirsutus*.

The invention thus also relates to a regulatory element which is active in Trametes or Polyporus and which comprises the sequence section from base 1–1192 present in SEQ ID NO: 1 or the sequence section from base 1–547 present in SEQ ID NO: 2 or the sequence section from base 1365–1542 present in SEQ ID NO: 3, and sequences homologous to this sequence section and having a homology of greater than 73%.

The present invention also provides a regulatory element which is active in Trametes and Polyporus comprising a sequence section selected from the group consisting of the sequence section from base 1–1192 present in SEQ ID NO: 1, the sequence section from base 1–547 present in SEQ ID NO: 2 and the sequence section from base 1365–1542 present in SEQ ID NO: 3 and regulatory elements derived thereof by base substitutions amounting to a sequence change of no more than 27%.

The selection media preferably used are those on which only *Trametes versicolor* transformants which have been transformed with a functionally expressed selection marker gene for the pyr G gene are able to grow. Preference is given to the minimal medium described in the 2nd example in the absence of uridine, on which pyr G-auxotrophic strains of *Trametes versicolor* are no longer able to grow, or can grow further only after addition of uridine.

Successful use of a DNA vector according to the invention containing the pyr G gene as selection system depends on efficient expression of the selection marker gene in Trametes transformants. Appropriate expression signals are necessary for efficient expression.

Expression signals from basidiomycetes bring about functional expression in *Trametes versicolor* with, surprisingly, considerably greater efficiency than the expression signals otherwise available from ascomycetes. For this reason, the pyr G selection marker gene in the DNA vectors according to the invention is preferably under the control of genetic regulatory elements from basidiomycetes, particularly preferably from those selected from the genera Trametes and Polyporus.

The pyr G gene is preferably under the control of the 5' promoter region upstream of it, and the 3' terminator region downstream of it. A DNA fragment in which the pyr G gene from *Schizophyllum commune* is under the control of the expression signals of the pyr G gene from *Schizophyllum commune* is described by Froeliger et al., Gene (1989) 83, 387–393. The pyr G gene may also be under the control of expression signals from basidiomycetes which differ from those of the pyr G gene. Expression signals which comply with this function include GAPDH promoters of filamentous fungi from the basidiomycetes class, such as, for example, *Coriolus hirsutus, Phanerochaete chrysosporium, Agaricus bisporus* or *Trametes versicolor*, the OCT promoter from *Coriolus hirsutus*, the promoter of laccase I or laccase III from *Trametes versicolor* and the terminator of the GAPDH gene from *Agaricus bisporus* or the terminators of the laccase I or laccase III gene from *Trametes versicolor*.

Particular preference is given to a vector which is described in the 3rd example, in which the pyr G gene from *Schizophyllum commune* is under the control of the expression signals of the pyr G gene from *Schizophyllum commune*.

The pyr G gene can be any gene which codes for a protein having the enzymatic activity of an orotidine-5'-phosphate decarboxylase. The pyr G gene preferably originates from a filamentous fungus from the basidiomycetes class, such as, for example, *Agaricus bisporus, Phanerochaete chrysosporium, Coriolus hirsutus, Polyporus pinsitus, Schizophyllum commune* or *Trametes versicolor*.

The pyr G gene from *Schizophyllum commune* and *Trametes versicolor* is particularly preferred.

The invention further relates to fungal strains selected from the genera Trametes and Polyporus which comprise a DNA vector according to the invention.

These fungal strains are capable of efficient expression and secretion of proteins.

The invention thus also relates in particular to filamentous fungi of the genus Trametes or Polyporus which comprise a DNA vector according to the invention.

The expressed and secreted proteins may be heterologous proteins or else homologous proteins.

Preference is given to a laccase. Such laccases are known from the strain *Trametes versicolor* for example (examples of laccase genes are the gene for laccase I: SEQ ID NO: 1, base 1193–3312, or the gene for laccase III: SEQ ID NO: 2, base 548–2542).

The invention thus also relates to a process for production of proteins which comprises employing the expression system according to the invention in a manner known per se for protein production, or comprises cultivating in a manner known per se a fungal strain which has been produced by the process according to the invention.

Such production processes are disclosed, for example, in CA: AN 96-203142, Eggert et al., Appl. Environ. Microbiol (1996) 62, 1151–1158, Martinez et al., Appl. Microbiol. Biotechnol. (1994) 41, 500–504, or WO 93/08272.

BRIEF DESCRIPTION OF THE DRAWINGS

In the drawings,

FIG. 2 shows that 7.5 kb-long vector in which the laccase III structural gene has been functionally linked to the promoter of the GAPDH gene and is called pLac3gap;

FIG. 3 shows the vector with a length of 9.1 kb which contains not only the laccase III gene but also the pyr G selection marker gene and is called pL3GpyrG; and FIG. 4 shows the sequence of genetic material for each of Primers A, B, C, D, E, F, G, and H, as well as for SEQ ID No: 12 and 13.

Figure 1:
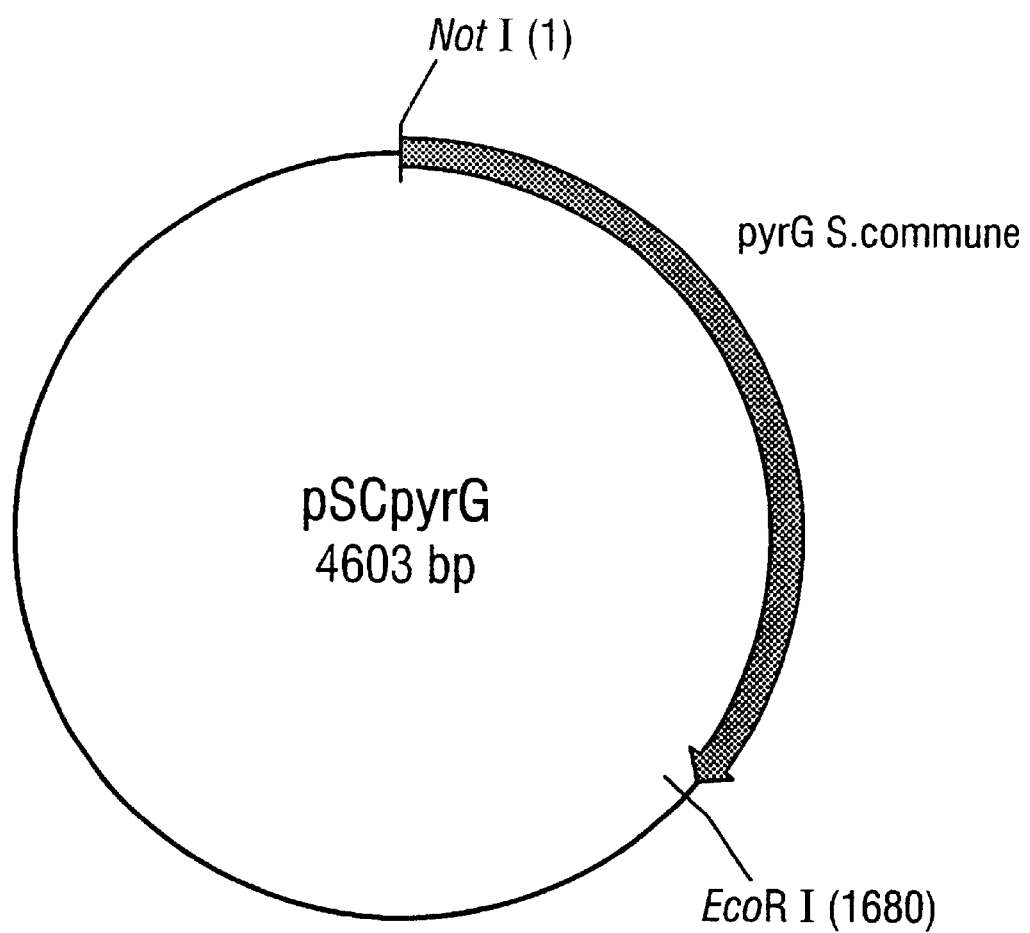
FIG. 1 shows the plasmid with the S. commune pyr G gene and is called pSCpyrG.

The following examples serve to illustrate the invention further. The standard methods used in the examples for treating DNA or RNA, such as treatment with restriction endonucleases, DNA polymerases, reverse transcriptase etc., and the standard methods such as transformation of bacteria, Southern and Northern Analysis, DNA sequencing, radiolabeling, screening and PCR technology were, unless indicated otherwise, carried out as recommended by the manufacturer or, if no manufacturer's instructions were available, in accordance with the prior art known from standard textbooks.

DETAILED DESCRIPTION OF PREFERRED EMBODIMENTS

1st EXAMPLE

Production of Trametes Protoplasts and Regeneration of Fungal Colonies

Protoplasts were obtained using the dikaryotic strains *Trametes versicolor* TV-1 (deposited at the DSMZ Deutsche Sammlung von Mikroorganismen und Zellkulturen GmbH, D-38124 Braunschweig under the number DSM 11523), *Trametes versicolor* 38070 (obtainable from the American Type Culture Collection, Rockville, Md. 20852 USA) and the monokaryotic strain *Trametes versicolor* F2 100 (deposited at the DSMZ Deutsche Sammlung von Mikroorganismen und Zellkulturen GmbH, D-38124 Braunschweig under the number DSM 11972). Mycelium from *Trametes versicolor* was initially obtained by growing on malt agar plates (3% malt extract, 0.3% peptone from soybean meal, 1.5% agar-agar, pH 5.0) at 28° C. for 7 days. Three pieces were punched out of the malt agar plates and used to innoculate 100 ml of sterile 1.5% malt extract medium (3% malt extract, 0.3% peptone from soybean meal, pH 5.0) in 500 ml Erlenmeyer flasks, or 125 ml of the sterile medium in 162 cm$^2$ cell culture vessels. The culture was incubated without shaking at 28° C. for 7 days until a dense mat of mycelium had grown in the culture liquid. The culture liquid was decanted off and fresh medium was added (30 ml for the mycelium from a 100 ml culture). The mycelium was homogenized with an Ultra Turrax (9500 rpm, 4 min) and incubated at 28° C. With shaking at 100 rpm for a further 18 h.

The mycelium suspension produced in this way was harvested by centrifugation at 1500 rpm (2000×g) for 5 min, and the mycelium obtained thereby was washed three times by suspending in 0.1 M $MgSO_4$, 0.6 M sucrose, 0.1 M phosphate, pH 5.8 (OMT medium) and subsequent centrifugation. The isolated mycelium was weighed and stored at 4° C. until treated with lytic enzyme.

Protoplasts were produced in the following way: mycelium from one flask was suspended in 15 ml of a freshly prepared and sterile-filtered solution of the lytic enzyme mixture Novozym 234 (3 mg/ml, Novo Nordisk, Bagsvaerd, Denmark) in OMT medium in a sterile Erlenmeyer flask. The mycelium resuspended in the enzyme solution was incubated at 30° C. in a shaking incubator (Infors) at a low speed (80 rpm) for 1 to 3 h. Formation of protoplasts was observed under the microscope during the incubation. Freely motile protoplasts were normally to be seen after 1 h. The end point of protoplasting was determined by visual inspection under the microscope, and the protoplasts were removed from the remaining mycelium by filtration through glass wool in a glass filter. The glass wool was carefully washed with ice-cold OMT medium. Protoplasts were isolated by centrifuging the suspension in a sterile sample vessel (2000 rpm; 2500×g, 4° C., 10 min). Further processing of the cells took place at 4° C. The protoplast pellet was washed by suspending in OMT medium and re-isolated by centrifugation. The washing step was repeated if required. The concentration of protoplasts was determined in a counting chamber under the microscope. The protoplast suspension was adjusted to a concentration of 1×10$^8$ protoplasts/ml for experiments for protoplast regeneration or for transformation.

For regeneration experiments, serial dilutions of the protoplast suspension were prepared and plated out on agar plates which contained 1.5% malt extract, 0.1% Trypticase peptone, 2% glucose, 1.5% agar and, for osmotic stabilization, 0.4 M mannitol. In this way, the proportion of viable cells was determined and it was tested whether the resulting protoplasts can be regenerated to mycelium-like growth. In the same way, the proportion of osmotically stable cells (for example mycelium fragments) was determined on plates without osmotic stabilization (without mannitol). The colonies obtained after incubation at 28° C. for 7 days were counted. The proportion of viable cells from a series of protoplast preparations was about 0.5%. These results show that it is possible to produce viable and regenerable protoplasts for transformation experiments from *Trametes versicolor*.

2nd EXAMPLE

Isolation of pyr G-deficient Mutants of *Trametes Versicolor*

Auxotrophic mutants of *Trametes versicolor* with a gene defect in pyrimidine metabolism (pyr mutants) were isolated by a method based on that described in Boeke et al., Methods Enzymol. (1987) 154, 164–175. The selective agent used was the genotoxic substance 5-fluoroorotic acid (FOA). Mutagenesis of *Trametes versicolor* protoplasts took place by UV treatment.

A: UV Mutagenesis:

The monokaryotic strain *Trametes versicolor* F2 100 described in the 1st example was used for the mutagenesis. Protoplasts of this strain were prepared as described in the 1st example.

A BioRad UV linker (5.8 W/cm$^2$, distance from the UV source 16 cm) was used for the mutagenesis. The number of protoplasts used for the mutagenesis was 8–10⁹. Protoplasts of *Trametes versicolor* were introduced into a Petri dish and irradiated with UV light for periods of various length. It emerged from this that, under the conditions described, irradiation for 60 sec. was optimal for subsequent selection of auxotrophic mutants.

B: Selection of Uridine-auxotrophic Mutants

The following minimal medium (MM) was used to select uridine-auxotrophic mutants:

| | |
|---|---|
| Glucose | 20 g/l |
| Agar | 15 g/l |
| Potassium dihydrogen phosphate | 1 g/l |
| Magnesium sulfate | 0.5 g/l |
| Disodium hydrogen phosphate | 0.1 g/l |
| Adenine | 27.5 mg/l |
| DL-phenylalanine | 0.15 g/l |
| L-asparagine | 2.5 g/l |
| Thiamine | 0.48 mg/l |
| Calcium chloride | 10 mg/l |
| Iron sulfate | 10 mg/l |
| Copper sulfate | 2 mg/l |
| Zinc sulfate | 1 mg/l |
| Manganese sulfate | 1 mg/l |
| pH 5.0, adjusted with sulfuric acid. | |

For osmotic stabilization of protoplasts, the MM was supplemented with 0.6 M sucrose (MMS). For liquid cultures, the MM was prepared without agar.

At the start, the MMS was supplemented with various concentrations of FOA and 10 mM uridine in order to characterize the growth properties of various Trametes strains on selective medium. It emerged that MMS with 1.5 mg/ml FOA and 10 mM uridine (selective MMS) completely suppressed the growth of the Trametes strains investigated.

Plates with selective MMS were inoculated with UV-mutagenized protoplasts (described in section A) and incubated at 28° C. for 21 days. In contrast to non-mutagenized protoplasts, growth of 35 colonies was observed. These potential pyr-deficient mutants were, in order to characterize the uridine-auxotrophic phenotype in detail, placed on MM plates, MM plates with 10 mM uridine and selective MM plates, and the growth was compared with the F2 100 initial strain. In this, three of the 35 picked colonies of Trametes mutants unambiguously showed a pyr-deficient phenotype. This is depicted in Table 1.

TABLE 1

Growth of Trametes versicolor mutants on various minimal media

| Strain | MM | MM + 10 mM uridine | MM + 10 mM uridine + 1.5 mg/ml FOA |
|---|---|---|---|
| F2 100 | + | + | − |
| F2 100B11 | − | + | + |
| F2 100B14 | − | + | + |
| F2 100B16 | − | + | + |

C: Identification of pyr G Mutants

Mutagenesis with FOA may lead either to mutants in the pyr F gene (orotate phosphoribosyltransferase) or in the required pyr G gene (orotidine-5'-phosphate decarboxylase). Differentiation of pyr G mutants and pyr F mutants took place by transformation with the pyr G gene from *Schizophyllum commune* (see 3rd example for the plasmid pSCpyrG).

After transformation with the plasmid pSCpyrG, colonies were observable on MM from the three pyr-deficient mutants detailed in Table 1. This indicates that all three mutants were deficient in the pyr G gene. The pyr G-deficient *Trametes versicolor* strain F2 100B11 could, however, be transformed with a frequency about 10-fold higher, so that this strain was used for the subsequent investigations.

The strains *Trametes versicolor* F2 100B11, F2 100B14 and F2 100B16 are the first pyr G-deficient strains of *Trametes versicolor* to be described to date. These pyr G-deficient strains can be used as host organisms for the previously undescribed transformation of *Trametes versicolor* and are thus novel and valuable host organisms for protein expression and protein secretion in filamentous fungi from the basidiomycetes class. Use of the strain F2 100B11 for this purpose is described in the following examples.

3rd EXAMPLE

Transformation of pyr G-auxotrophic *Trametes Versicolor* Strains with the pyr G Gene from *Schizophyllum Commune*

A: Isolation of the pyr G Gene from *Schizophyllum Commune*

The isolation and DNA sequence of the pyr G gene from *Schizophyllum commune* (referred to as URA1 gene in the publication) is described in Froeliger et al., Gene (1989) 83, 387–393. Mycelium of *Schizophyllum commune* (strain ATCC 44201, purchased from the ATCC American Type Culture Collection, 12301 Parklawn Drive, Rockville, Md. 20852-1776, USA) was produced in malt extract medium as described in the 1st example for *Trametes versicolor*. Isolation of chromosomal DNA likewise followed the method for *Trametes versicolor* and is described in the 4th example. The pyr G gene was amplified by PCR from chromosomal DNA of *Schizophyllum commune*. This was done by using primers A and B (derived from the sequence published in Froeliger et al., Gene (1989) 83, 387–393), with which it was possible to amplify not only the coding region but also promoter and terminator sequences.

Primer A: (SEE FIG. 4) SEQ ID NO: 4

Primer B: (SEE FIG. 4) SEQ ID NO: 5

PCR amplifications were carried out in accordance with the prior art and the statements of the manufacturer (PCR kit from Strategene): 200 ng of chromosomal *S. commune* DNA were employed in a 100 μl PCR which contained buffers provided by the manufacturer and, in addition, 1.25 U of Pfu polymerase, 0.2 mM of each of the four dNTPs (dATP, dCTP, cGTP, dTTP) and 100 pmol of each of primers A and B. The further conditions for the specific amplification of the required PCR product were: 5 min at 94° C. followed by 25 cycles of 1 min at 94° C., 1.5 min at 50° C. and 2.5 min at 72° C. and, finally, 5 min at 72° C. The required PCR product with a size of about 1.6 kb was purified by agarose gel electrophoresis and cloned into the PCR-Script SK(+) vector (Strategene) and transformed into *E. coli*. The plasmid was isolated from transformed *E. coli* cultures. DNA sequence analysis of the insert from a positive clone confirmed that the *S. commune* pyr G gene had been amplified. The plasmid with the *S. commune* pyr G gene was called pSCpyrG (FIG. 1).

B: Transformation of *Trametes versicolor* pyr G-deficient Strains

Protoplasts of *T. versicolor* F2 100B11 (see 2nd example) were prepared by the method described in the 1st example. In this case, the medium for culturing the auxotrophic strain had been supplemented with 10 mM uridine. The vector pSCpyrG (described in section A) was used for transformation.

As described in the 1st example, protoplasts of *Trametes versicolor* F2 100B11 were prepared and suspended at a final concentration of 10⁸/ml. 0.1 ml aliquots of the protoplasts were mixed with in each case 10 µg of plasmid DNA in incubation vessels with a volume of 12 ml, and incubated on ice for 30 min. Then, slowly and with repeated mixing, 1.25 ml of a PEG4000 solution were added to the transformation mixture. After incubation at room temperature for a further 20 min, the reaction vessels were filled up with the OMT medium described in the 1st example, mixed and centrifuged at 2000×g and 4° C. for 10 min. The pellets were resuspended and plated out on osmotically stabilized MMS plates without uridine (described in the 2nd example). The plates were incubated at 28° C. for 14 days and examined for growth of colonies. Transformation rates of 0.1–3 transformants/µg of plasmid DNA were achieved in various experiments.

C: Purification of the Transformants

Mycelium of the resulting transformants was picked and purified by plating out on fresh MM plates. In this case, the inoculum was placed as a spot in the middle of the plate. After incubation at 28° C. for 7 to 14 days, radial mycelial growth was observed. This purification process was repeated, taking the mycelium for the inoculum from the edge of the first purification plate. MM plates were then inoculated anew with inoculum from the second purification plate and incubated at 28° C. until mycelium growth covered the plates.

D: Analysis of the Transformants

Transformants of *Trametes versicolor* were investigated by Southern blot analysis for integration of the plasmid pSCpyrG. This was done by producing mycelium of various transformants and, as a control, the pyr G-deficient strain F2 100B11 in liquid culture (see 1st example, malt extract medium, with addition of 10 mM uridine). Chromosomal DNA was isolated from the isolated mycelium as described below in the 4th example.

1 µg of chromosomal DNA from each of the investigated strains and 100 ng of the plasmid pSCpyrG were cut by double digestion with Not I and Eco RI and then separated by agarose gel electrophoresis, blotted onto nylon filters (Qiagen) and hybridized with a radiolabeled DNA probe specific for the pyr G gene from *Schizophyllum commune*.

The DNA probe was prepared by cutting the plasmid pSCpyrG by a double digestion with Not I and Eco RI and isolating the resulting 1.4 kb-long DNA fragment of the pyr G gene by preparative gel electrophoresis. The 1.6 kb-long pyr -c G-specific DNA fragment was radiolabeled with α-[³²P]-dATP ("Random Priming" Kit, Boehringer Mannheim). Free radio-activity was removed by chromatography on Sephadex G25 (Pharmacia). The specific activity of the radiolabeled DNA probe was 1×10⁷ cpm/µg DNA. The temperature for hybridization of the DNA blotted onto nylon filters with the radiolabeled DNA probe was 60° C. Otherwise, the conditions described in the specialist literature for Southern blots were complied with. Southern blots were analyzed by autoradiography. In this it was possible to detect the 1.6 kb-long pyr G-specific DNA fragment only in the transformants but not in the uridine-auxotrophic strain F2 100B11. This result confirms that on transformation of the uridine-auxotrophic *Trametes versicolor* strain F2 100B11 the plasmid pSCpyrG had been integrated into the genome and led to productive expression of the selection marker gene pyr G, whereby the uridine auxotrophy of this strain was complemented. Surprisingly, it was also found for the first time that the expression signals of the pyr G gene from the basidiomycete *Schizophyllum commune* are also able to function in *Trametes versicolor*.

4th EXAMPLE

Cloning of *T. Versicolor* Laccase Genes

A: Production of a Chromosomal Gene Bank from *Trametes Versicolor*

Genomic DNA from *T. versicolor* was isolated from the mycelium from a shaken flask culture. 1 g of mycelium of *T. versicolor* was ground to a fine powder using a mortar and pestle in the presence of liquid nitrogen. The powder was placed in a sterile sample vessel and immediately mixed with 5 ml of extraction solution (0.1 M tris-HCl, pH 8.0, 0.1 M EDTA, 0.25 M NaCl, 0.6 mg/ml proteinase K) and 0.5 ml of a 10% (w/v) sodium lauroylsarcosine solution. After incubation at 50° C. for at least 2 h, the mixture is mixed with 0.85 ml of 5 M NaCl and 0.7 ml of a 10% (w/v) CTAB solution in 0.7 M NaCl and incubated at 65° C. for 30 min. After addition of 7 ml of a chloroform/-isoamyl alcohol mixture (24:1), the mixture is shaken and the two phases are separated by centrifugation. The aqueous phase is removed, and chromosomal DNA is precipitated by adding 0.6 part by volume of isopropanol. The precipitated DNA is subsequently purified on a column (Qiagen Genomic Tip). It was possible in this way to isolate 0.5 mg of chromosomal DNA from 16 g of mycelium.

To produce the chromosomal gene bank, 90 µg of chromosomal DNA from *Trametes versicolor* TV-1 were cut in a partial digestion with Sau 3A and fractionated by agarose gel electrophoresis. The chromosomal DNA fragments were isolated in the size range of 5–20 kb and greater than 20 kb and cloned in each case into lambda phages previously cut with Bam HI (Strategene cloning system). 4–10⁴ phages/µg of vector DNA were present of the 5–20 kb DNA fraction and 5×10⁴ phages/µg of vector DNA were present of the DNA fraction greater than 20 kb. The phages were amplified by infection of the *E. coli* strain XL-1 Blue MRF'.

B: Isolation of a laccase-specific DNA probe

A DNA probe for isolating laccase genes was produced by PCR amplification from *T. versicolor* genomic DNA using degenerate primers. The degenerate primers were constructed on the basis of a comparison of the sequences of known laccase genes. The amino acid sequences of the laccase genes, present in the EMBL gene database, of *Neurospora crassa, Coriolus hirsutus, Phlebia radiata, Agaricus bisporus* and a filamentous fungus not characterized in detail from the subclass of basidiomycetes were compared. It was possible by the sequence comparison to identify four peptides with a length of from 5 to 7 amino acids which were completely conserved in all the laccases. These peptides were translated back into DNA, taking account of degenerate codons, in order to produce degenerate primers. The primers had the following sequences:

Primer C: (SEE FIG. 4) SEQ ID NO: 6
Primer D: (SEE FIG. 4) SEQ ID NO: 7
Primer E: (SEE FIG. 4) SEQ ID NO: 8
Primer F: (SEE FIG. 4) SEQ ID NO: 9

Primers E and F contained in the 5' region a Bam HI cleavage site (underlined) and, connected thereto, in each case the appropriate degenerate laccase sequence. PCR amplifications were carried out in accordance with the prior art and the statements by the manufacturer (PCR kit from Perkin Elmer): in a first PCR, 200 ng of chromosomal *T. versicolor* DNA were employed in a 100 µl PCR which contained the buffer provided by the manufacturer and, in addition, 1.25 U of Taq polymerase, 1.25 mM MgCl₂, 0.2 mM of each of the four dNTPs (DATP, dCTP, cGTP, dTTP) and in each case 100 pmol of primers C and D. The further conditions for the specific amplification of the required.

PCR product were: 5 min at 94° C. followed by 7 cycles of 0.5 min at 94° C., 1 min at 40° C. and 2.5 min at 60° C., and 30 cycles of 0.5 min at 94°C., 1 min at 50° C. and 2.5 min at 72° C. 1 µl of the first PCR was employed in a second PCR which additionally contained 1.25 U of Taq polymerase, 1.25 MM MgCl$_2$, 0.2 mM of each of the four dNTPs and in each case 100 pmol of primers E and F. The further conditions for the specific. amplification of the required PCR product were: 5 min at 94° C. followed by 7 cycles of 0.5 min at 94° C., 1 min at 40° C. and 2.5 min at 60° C. and 30 cycles of 0.5 min at 94° C., 1 min at 50° C. and 2.5 min at 72° C. A PCR product of about 1.1 kb was obtained. The PCR product was purified by agarose gel electrophoresis, cut with the restriction enzyme Bam HI and cloned into a Bam HI-cut pUC18 vector and transformed into E. coli. The plasmid was isolated from transformed E. coli cultures. DNA sequence,analysis at the 5' and 3' ends confirmed that the cloned DNA fragment was the fragment of a laccase gene.

To prepare the DNA probe for screening laccase genes, the laccase-specific PCR fragment was cut out by treatment with Bam HI, isolated by agarose electrophoresis and radiolabeled with α-[$^{32}$P]-dATP ("Random Priming" Kit, Boehringer Mannheim). Free radioactivity was removed by chromatography on Sephadex G25 (Pharmacia). The specific activity of the radiolabeled DNA probe was $1 \times 10^7$ cpm/µg DNA.

C: Isolation of Chromosomal Laccase Genes.

The chromosomal gene bank from *Trametes versicolor* TV-1 described in section A was used. Screening for genomic laccase genes was carried out in accordance with the prior art. In a first screening round, cells of *E. coli* XL-1 Blue MRF' were first cultivated on 10 Petri dishes and then infected with 50,000 phages of the chromosomal gene bank (5–20 kb fraction see 4th example) per Petri dish. After incubation at 37° C. overnight, the newly formed phages were transferred to nylon filters (Strategene). The filters were then hybridized in accordance with the manufacturer's recommendations with the radio labeled laccase-specific probe (see section B). The hybridization temperature was 45° C. in a hybridization buffer containing 50% formamide. Positive clones were picked and purified by repeating the screening process. After three rounds of isolation in the screening, 20 strongly hybridizing phage clones were isolated and were recloned into the pBK CMV vector (Strategene) by in vivo excision using a method of the manufacturer (Stratagene) Analysis of the clones by digestion with restriction endonucleases and DNA sequencing revealed that 15 of the 20 clones were laccase clones. Two different laccase clones were obtained. The two laccase genes were called laccase I and laccase III. The plasmids with the two laccase genes were called pLac100 (SEQ ID No: 1) and pLac300 (SEQ ID No: 2). Both laccase genes comprised not only the sequence information for the structural gene (coding region) but also sequence information in the region 5' in front of the ATG start codon (promoter region) and sequence information in the region 3' after the stop codon (terminator region). These are novel genetic regulatory elements for *Trametes versicolor* which can be used to produce DNA vectors for gene expression in filamentous fungi from-the basidiomycetes class. Table 2 summarizes the corresponding sequence regions in SEQ ID No: 1 (laccase I gene) and SEQ ID No: 2 (laccase III gene).

TABLE 2

Genetic elements in SEQ ID No: 1 and SEQ ID No: 2

|  | SEQ ID No: 1 laccase I gene | SEQ ID No: 2 laccase III gene |
| --- | --- | --- |
| Promoter | bp 1–1192 | bp 1–547 |
| Structural gene (with introns) | bp 1193–3312 | bp 548–2542 |
| Terminator | bp 3313–7986 | bp 2542–5762 |

5th EXAMPLE

Cloning of the *T. Versicolor* GAPDH Gene

A. Isolation of a GAPDH DNA Probe from *Trametes Versicolor*

The strain *Trametes versicolor* TV-1 (see 1st example) was used. Cultivation of TV-1 and isolation of chromosomal DNA took place as described in the 1st example and 4th example respectively. Primers for PCR amplification of a GAPDH-specific gene fragment were constructed on the basis of the published DNA sequences of the GAPDH gene from *Phanerochaete chrysosporium* (M. C. Harmsen et al. (1992), Curr. Genet. 22, 447–454) and of the GAPDH gene from *Coriolus hirsutus* (JP 9-47289). The primers had the following DNA sequences:

Primer G: (SEE FIG. 4) (SEQ ID NO: 10)
Primer H: (SEE FIG. 4) (SEQ ID NO: 11)

PCR amplifications were carried out in accordance with the prior art: in a PCR, 200 ng of chromosomal *Trametes versicolor* DNA were employed in a 100 µl PCR which contained the buffer provided by the manufacturer and, in addition, 1.25 U of Taq polymerase, 1.25 mM MgCl$_2$, 0.2 mM of each of the four dNTPs (dATP, dCTP, cGTP, dTTP) and in each case 100 pmol of primers G and H. The further conditions for the specific amplification of the required PCR product were: 5 min at 94° C. followed by 7 cycles of 0.5 min at 94° C., 1 min at 47° C. and 1 min at 72° C., and 30 cycles of 0.5 min at 94° C., 1 min at 50° C. and 1 min at 72° C. A PCR product of about 0.43 kb was obtained. The PCR product was purified by agarose gel electrophoresis, cloned into the vector PCR-Script SK(+) (Stratagene) and transformed into *E coli*. The plasmid was isolated from transformed *E. coli* cultures. DNA sequence analysis of the 5' and 3' ends confirmed that the cloned DNA fragment was the fragment of the *P. chrysosporium* GAPDH gene.

To prepare the DNA probe for screening laccase genes, the laccase-specific PCR fragment was cut out by treatment with Not I and Eco RI, isolated by agarose electrophoresis and radiolabeled with α-[$^{32}$P]-dATP ("Random Priming" Kit, Boehringer Mannheim). Free radioactivity was removed by chromatography on Sephadex G25 (Pharmacia). The specific activity of the radiolabeled DNA probe was $1 \times 10^7$ cpm/µg DNA.

B: Isolation of a Chromosomal GAPDH Gene from *T. versicolor*:

The chromosomal gene bank from *Trametes versicolor* TV-1 described in section A of the 4th example was used. Screening for the chromosomal GAPDH gene was carried out in accordance with the prior art. In a first screening round, cells of *E. coli* XL-1 Blue MRF' were first cultivated on 10 Petri dishes and then infected with 50,000 phages of the gene bank (5–20 kb fraction see 4th example) per Petri dish. After incubation at 37° C. overnight, the newly formed phages were transferred to nylon filters (Strategene). The filters were then hybridized in accordance with the manufacturer's recommendations with the radiolabeled GAPDH-specific probe (see section A). The hybridization temperature was 58° C. The washing temperature was 58° C. 28 positive clones were picked. 10 of these clones were purified by repeating the screening process. After three rounds of isolation in the screening, 9 strongly hybridizing phage clones were isolated and were recloned into the pBK CMV vector (Stratagene) by in vivo excision using a method of the manufacturer (Stratagene). Analysis of the clones by digestion with restriction endonucleases and DNA sequencing revealed that all nine clones were GAPDH clones. It was possible to divide the nine clones into 6 classes on the basis of a restriction analysis. The DNA sequence of the available coding region (SEQ ID NO: 3, bp 1543–2387) and about 1.5 kb of the promoter region 5' in front of the ATG start codon (SEQ ID NO: 3, bp 1–1542) was determined-for the clone with the largest GAPDH gene fragment, called pGAPTV (SEQ ID NO: 3).

6th EXAMPLE

Functional Linkage of the GAPDH Promoter to the Laccase III Gene

A: Cloning of the Laccase III Gene into the pBluescript Vector

For further processing, the laccase III gene from pLac300 was recloned into the pBluescript vector. This was done by isolating the laccase III gene as 3.5 kb Spe I-Sma I fragment from the pBK CMV vector obtained in the 4th example and subcloning into the pBluescript vector which had previously been cut.with Spe I and Sma I. The resulting 6.5 kb plasmid was called pLac301. For linkage to the GAPDH promoter, pLac301 contained a Not I cleavage site originating from pBluescsript, via which it was possible to produce a functional linkage to the 3' end of the GAPDH promoter (see section B of this example).

B: Functional Linkage of the ATG Translation Start Codon of the Laccase III Gene to the GAPDH Promoter The 1.5 kb-long promoter region of the GAPDH gene isolated in the 4th example was isolated from pGAPTV (SEQ ID NO: 3, see 5th example) as Not I-BspLU11 I fragment. In this case the Not I cleavage site originated from the pBK CMV vector portion and the BspLU11 I cleavage site originated from the ATG start codon of the GAPDH gene.

Vector pLac301 was cut with Not I and partially with BspLU11 I, and the 6 kb vector fragment which had been shortened by the 0.55 kb promoter portion of the laccase III gene was isolated.

The 1.5 kb-long Not I-BspLU11 I GAPDH promoter fragment was ligated to the 6 kb Not I-BSPLU11 I vector fragment from pLac301 and transformed into E. coli. The plasmid was isolated from transformed E. coli cultures. Positive clones were examined by restriction analysis and DNA sequencing. The 7.5 kb-long vector in which the laccase III structural gene had been functionally linked to the promoter of the GAPDH gene was called pLac3gap (FIG. 2). In pLac3gap, the GAPDH promoter region was functionally linked via a BspLU11 I cleavage site to the ATG translation start codon of the laccase III gene.

C: Incorporation of the Selection Marker Gene pyr G into the Vector pLac3gap

For preparation, an additional Not I cleavage site was incorporated into the Eco RI cleavage site originating from the polylinker of the pCR script SK(+) vector in the vector pSCpyrG. This was done by using the adaptor A with the following sequence.

(SEE FIG. 4) SEQ ID NO: 12
(SEE FIG. 4) SEQ ID NO: 13

Vector pSCpyrG was linearized with Eco RI and 5'-dephosphorylated with alkaline phosphatase. The linearized pSCpyrG vector was then ligated with various concentrations of the adaptor A and transformed into E. coli. Positive clones were identified by digestion of the isolated plasmid DNA with Not I, in which case the 1.6 kb fragment of the Schizophyllum commune gene fragment was liberated due to introduction of a second Not I cleavage site. This vector was called pSCpyrG-Not.

The vector pSCpyrG-Not was treated with Not I, and the 1.6 kb pyr G fragment liberated in this way was isolated by agarose gel electrophoresis.

The vector pLac3gap was linearized with Not I, and the 7.5 kb fragment was then treated with alkaline phosphatase in order to eliminate the 5'-phosphate groups.

The 1.6 kb pyr G fragment was cloned into pLac3gap which had been linearized with Not I and dephosphorylated and was transformed into E. coli, and the plasmid DNA was isolated from positive E. coli transformants. Positive transformants contained the 1.6 kb pyr G gene fragment. Clones in which the orientation of the pyr G selection marker gene was the same as that of the laccase III gene were identified by restriction analysis. The vector with a length of 9.1 kb which contained not only the laccase III gene but also the pyr G selection marker gene was called pL3GpyrG (FIG. 3).

7th EXAMPLE

Overproduction of Laccase III in Trametes Versicolor

A. Transformation of T. Versicolor

T. versicolor protoplasts were produced by the method described in Example 1 and transformed with the vector pL3GpyrG described in the 6th example.

Protoplasts of the pyr G-deficient strain Trametes versicolor F2 100B11 were produced as described in the 2nd example and were suspended at a final concentration of $10^8$/ml. 0.1 ml aliquots of the protoplasts were incubated with 10 μg of DNA of the plasmid pL3GpyrG in incubation vessels with a volume of 12 ml on ice for 30 min. Then, slowly and with repeated mixing, 1.25 ml of a PEG4000 solution were added to the transformation mixture. After incubation at room temperature for a further 20 min, the reaction vessels were filled up with the OMT medium described in the 2nd example, mixed and centrifuged at 2000×g and 4° C. for 10 min. The pellets were resuspended and plated out on osmotically stabilized MM without uridine (described in the 2nd example). The plates were incubated at 28° C. for 14 days and examined for growth of colonies. Transformation rates of 0.5–3 transformants/μg of plasmid DNA were achieved in various experiments.

B: Purification of the Transformants

Mycelium of the resulting transformants was picked and purified by plating out on fresh plates with MM selection medium without uridine. In this case, the inoculum was placed in the form of a spot in the middle of the plate. After incubation at 28° C. for 7 to 14 days, radial mycelial growth was observable. This purification process was repeated, taking the mycelium for the inoculum from the edge of the first purification plate. Selective plates were then inoculated anew with inoculum from the second purification plate and, after the plates were completely covered with mycelial growth, the laccase production was checked in shaken flask cultures.

C: Culturing in a Shaken Flask

For culturing in a shaken flask, 2 cm$^2$ of mycelium were punched out of a plate showing full growth and were crushed under sterile conditions and used to inoculate a preculture of 50 ml (in a 250 ml Erlenmeyer flask) of malt extract medium (see 1st example). The preculture was incubated at 28° C. while shaking at 120 rpm for 6 days. On the sixth day, the preculture was homogenized with an Ultra Turrax at 9500 rpm for 30 sec and used to inoculate 250 ml of main culture medium (for composition, see MM in the 1st example) in a 1 l Erlenmeyer flask. The main culture was then again incubated at 28° C. while shaking at 120 rpm. Laccase production was measured each day after the second day of culturing. Laccase activity was determined photometrically using the substrate ABTS (2,2'-azinobis(3-ethylbenzothiazoline-6-sulfonic acid)) at 420 nm. Extinction coefficient of ABTS at 420 nm $\epsilon_{420}$: $3.6\times10^4$ [l×mol$^{-1}$×cm$^{-1}$]. In this, 1 U of laccase activity corresponded to the conversion of 1 μmol of ABTS/min at 37° C. and a pH of 4.5. The maximum laccase production in the shaken flask cultures was reached 8–10 days after starting the main culture. Table 3 shows a comparison of various transformants with the untransformed starting strain Trametes versicolor F2 100. For the untransformed strain F2 100, laccase production was additionally determined after induction with the inducer 2,5-xylidine described in the literature (Yaver et al., Applied and Environmental Microbiology (1996) 62, 834–841). As is evident from Table 3, laccase production in the shaken flask was increased with the best transformants of the strain F2 100 by a factor of 12 (without induction) and by a factor of 5 (with induction) compared with the untransformed starting strain.

TABLE 3

| Trametes versicolor strain | Maximum laccase production (U/ml) |
| --- | --- |
| F2 100 | 3.8 |
| F2 100/xylidine* | 9.6 |
| TV lac3gap-2 | 31.2 |
| TV lac3gap-3 | 36.7 |
| TV Lac3gap-6 | 45.8 |
| TV Lac3gap-8 | 22.3 |
| TV Lac3gap-11 | 46.1 |
| TV Lac3gap-15 | 15.1 |
| TV Lac3gap-17 | 42.9 |
| TV Lac3gap-21 | 30.6 |
| TV Lac3gap-25 | 18.3 |

*Induction took place three days after starting the main culture by adding 2,5-xylidine (final concentration 1.5 mM).

---

What is claimed is:

1. An expression system for production of a protein in a filamentous fungus consisting of
   a) a host organism selected from the group of genera consisting of Trametes and Polyporus;
   b) a DNA vector which comprises a selection marker gene which codes for a protein which, after transformation of the host organism, allows selection of positive transformants and is selected from the group consisting of antibiotic resistance genes, of genes which encode proteins which are capable of a color-forming reaction, and of genes which complement a genetic defect in the host organism (auxotrophy), where expression of the selection marker gene is controlled by at least one genetic regulatory element which is active in the host organism; and
   c) a DNA vector selected from the group consisting of (1) a DNA vector which comprises a gene which codes for the protein to be produced, where expression of this gene and, also secretion of the protein thus produced is controlled by a genetic regulatory element which is active in the host organism,
      said genetic regulatory element which is active in Trametes or Polyporus comprises a sequence section which is selected from the group consisting of the sequence section from base 1–1192 present in SEQ ID NO: 1,
   the sequence section from base 1–547 present in SEQ ID NO: 2, and the sequence section from base 1365–1542 present in SEQ ID NO: 3,
   and (2) the DNA vector which comprises a selection marker gene, and the DNA vector which comprises the gene which codes for the protein to be produced are present as one DNA vector, and
   said DNA vector which comprises a gene which codes for the protein to be produced, where expression of this gene and, also secretion of the protein thus produced is controlled by a genetic regulatory element which is active in the host organism,
   said genetic regulatory element which is active in Trametes or Polyporus comprises a sequence section which is selected from the group consisting of the sequence section from base 1–1192 present in SEQ ID NO: 1,
   the sequence section from base 1–547 present in, SEQ ID NO: 2, and the sequence section from base 1365–1542 present in SEQ ID NO: 3.

2. An expression system as claimed in claim 1, wherein the host organism is a monokaryotic strain selected from the group consisting of the genus Trametes and the genus Polyporus.

3. An expression system as claimed in claim 1, wherein the host organism is *Trametes versicolor*.

4. An expression system as claimed in claim 1, wherein the host organism has a defect in the orotidine-5'-phosphate decarboxylase gene (pyr G gene) and is auxotrophic for uridine, and the selection marker gene is a pyr G gene.

5. An expression system as claimed in claim 1, wherein the genetic regulatory element active in the host organism is selected from the group consisting of the promoter, terminator elements for a glyceraldehyde-3-phosphate dehydrogenase gene (GAPDH gene), and the promoter and terminator elements for a laccase gene.

6. An expression system as claimed in claim 1, wherein the protein to be expressed is a laccase.

7. A DNA vector which comprises at least one selection marker gene which codes for a protein which, after transformation into a host organism selected from the group of genera consisting of Trametes and Polyporus, allows selection of positive transformants, wherein the selection marker gene is selected from the group consisting of antibiotic resistance genes, genes which encode proteins which are capable of a color-forming reaction, and genes which complement a genetic defect in the host organism (auxotrophy), and wherein the selection marker gene is controlled by at least one genetic regulatory element active in the host organism, and said genetic regulatory element which is active in Trametes or Polyporus comprises a sequence section selected from the group consisting of the sequence section from base 1–1192 present in SEQ ID NO: 1, the sequence section from base 1–547 present in SEQ ID NO: 2, and the sequence section from base 1365–1542 present in SEQ ID NO: 3.

8. A regulatory element which is active in Trametes or Polyporus comprising a sequence section selected from the group consisting of the sequence section from base 1–1192 present in SEQ ID NO: 1, the sequence section from base 1–547 present in SEQ ID NO: 2, and the sequence section from base 1365–1542 present in SEQ ID NO: 3.

9. A process for producing fungal strains which are capable of efficient expression and secretion of proteins, comprising using as host strain a fungus selected from the group of genera consisting of Trametes and Polyporus which has a uridine-auxotrophic gene defect which is transformed with a DNA vector which has a gene for complementation of the auxotrophic gene defect in the host strain;

selecting from a transformation mixture, clones transformed with the DNA vector by selection for complementation of the auxotrophic gene defect, where expression of the gene for complementation of the auxotrophic gene defect in the host strain is controlled by a genetic regulatory element which is active in the host strain; and said genetic regulatory element which is active in Trametes or Polyporus comprises a sequence section selected from the group consisting of the sequence section from base 1–1192 present in SEQ ID NO: 1, the sequence section from base 1–547 present in SEQ ID NO: 2, and the sequence section from base 1365–1542 present in SEQ ID NO: 3.

10. A process for production of a protein, which comprises utilizing an expression system as claimed in claim 1 for protein production.

11. A process for production of proteins, which comprises cultivating a fungal strain which has been prepared by a process as claimed in claim 9.

* * * * *

SEQUENCE LISTING

<160> NUMBER OF SEQ ID NOS: 13

<210> SEQ ID NO 1
<211> LENGTH: 7986
<212> TYPE: DNA
<213> ORGANISM: Trametes versicolor

<400> SEQUENCE: 1

```
agcttgcgcg tccgcatcgc ctctaccatg ggaaagaggc aataacgcgg cccccgccgg      60
gaatagcgct atgtggcccc gtccccggag ctctcaaagc ctgggatctc gtctcttcat     120
cattccaagc ggtcgacgct catgtcggac aacgagcccg actcttggct agcctggaaa    180
ggcccgtgtt cggagacaag acctaccccc ggcataggga gcgggacaga tgtgccggag    240
gatgagaacc cgctgggtaa ggagggccag atacatgtgg gcggcgacgc cacgggdaca    300
tgggcgtttc cgcttaaccc ctcttctttc ctttcttggc ggaggatcct gcctcagaat    360
catcatgctc gcccggccga aagctctggc ctcccgtcct tcccactcta aacgtacgtg    420
accatcggga tgatcagtct ggccatggat gcgtcaaacc gaccttgcag tgctcaaaca    480
tgtaactgac gcggctcttg cagggcgata ctctccgctc tcgttggctg cgtcgactac    540
cttgtacacc caagatagcg cgtttcctgc ccaaatagcg gtcgaaatgc ccccgcgatc    600
ctctcccgag tactagcatc ccaaccgatc cgacccgctc gaacagctca tgaattaccg    660
aatccatgga cccgcccatc ggcgtagtca gttacgatca agcagacctg aagggtcttc    720
cagtgcactg ggctaccagc gccatccggc gctgcatcta cgcgccttcc cggcgcatta    780
tagacgcatg tggccaccac aggcctgctg gctctcttcc gccaccagcg cggcgcacaa    840
accgtgggac ccagcacact cccgcccact ctcacactgg ccagattcgc gcgaccgccg    900
cctttcaggc ccaaacagat ctggcaggtt tcgatggcgc acgccgtcgt gcctgccgga    960
```

-continued

```
ttcaattgtg cgccagtcag gcatccggat gcctctacca gcgcggttga ctggaagaga    1020
acaccgaggt catgcattct ggccaagtgc ggccagagga ccgcccgctg gtgcgggtac    1080
ttaaagggcg gcgcgggag gcctgtcgac caagctcaag ctcgccttgg gttcccagtc    1140
tccgccatcc tcctcctccc ccacacactc gctccatatc acgctcggcg ccatgggtct    1200
gcagcggttc agcttcttcg tcaccctcgc gctcgtcgct cgctctcttg cagccatcgg    1260
gccggtggcg agcctcgtcg tcgcgaacgc ccccgtctcg cccgacggct tccttcggga    1320
tgccatcgtg gtcaacggcg tggtcccttc cccgctcatc actgggaaga aggtcggcgt    1380
gttcgttgtc gtcctactcc tttactgaca gcgatctaca gggagaccgc ttccagctca    1440
acgtcgtcga caccttaacc aaccactcca tgctcaagtc cactagtatc gtaagtgtga    1500
cgatccgaat gtgacatcat ccggggctaa ttaaccgcgc acagcactgg cacggcttct    1560
tccaggcagg caccaactgg gcagacggac ccgcgttcgt caaccagtgc cctattgctt    1620
ccgggcattc attcctgtac gacttccatg tgcccgacca ggcaggtaag cagtctttgt    1680
tgtgatcctc gtgtgatgca atgttctcat gctccgacgt gatcgacagg gacgttctgg    1740
taccacagtc atctgtctac gcaatactgt gacgggctgc gaggaccgtt cgtcgtgtac    1800
gaccccaagg atccgcacgc cagccgctac gatgttgaca acggtacgtg cgccacggag    1860
tatatcacac agcatgcgtt gacgtcgggc caacagagag cacggtcatc acgttgaccg    1920
actggtacca caccgctgcc cggctcggtc ccaggttccc gtaagctcgc aatggattag    1980
tttttacgga ttatttgctt atgttgcgtc gatagactcg gcgcggacgc cacgctcatc    2040
aatggtcttg ggcggtcggc ctccactccc accgccgcgc ttgctgtgat caacgtccag    2100
cacggaaagc ggtgagcatt ctcttgcatg ccatttcaat gctctaaatt gacctatcgg    2160
caccacgcag ctaccgcttc cgtctcgttt cgatctcgtg cgacccgaac tacacgttca    2220
gcatcgacgg gcacaatctg accgtcatcg aggtcgacgg tatcaacagc cagcctctcc    2280
ttgtcgactc tatccagatc ttcgccgcgc agcgctactc ctttgtggta tgtcctgccc    2340
tcttggtgct tccaaagtgg cctcgctcac ccattctttt agttgaatgc gaaccaaacg    2400
gtcggcaact actgggtccg tgcgaacccg aacttcggaa cggttgggtt cgccgggggg    2460
atcaactccg ccatcctgcg ctaccaaggc gcaccggtcg ccgagcctac tacgacccag    2520
acgccgtcgg tgatcccgct cattgagacg aacttgcacc cctcgctcg catgcctgtg    2580
gtacgtttct ttcattcata taatgaccgc gtcgccgagc tcaccgcgcg ctcctatcca    2640
gcctggcagc ccgacgcccg gaggtgtcga caaggcactg aacctggcct tcaacttcgt    2700
gagtgtctat accgcccaat ttggggtcct cgtactgatc atgcggcgca atagaacggc    2760
accaacttct ttatcaacaa cgcgtctttc acaccaccga cagtccccgt gctcctccag    2820
atcctgagcg gtgcgcagac cgcacaggaa ctcctccctg caggctccgt ctaccgctc    2880
ccggcccact ccaccatcga gatcacgctg cccgcgaccg cactagcccc aggcgcgccg    2940
caccccttcc acctgcacgg tgtacgtccc cctccttctc tccctcctcg cacaagtgct    3000
cacgtccagc ccctctagca cgcgttcgcg gtcgtccgca gcgcaggcag cactacgtat    3060
aactacaacg acccgatctt ccgcgacgtc gtgagcaccg gcacgcccgc cgcgggcgac    3120
aacgtcacga tccgcttcca gacggacaac cccgggccgt ggttcctcca ctgccacatc    3180
gacttccacc tcgaggcggg cttcgcgatc gtgttcgcgg aggacgttgc ggatgtgaag    3240
gcggcgaacc cggtcccaaa ggcgtggtcg gacctgtgcc cgatctacga cgggctgagc    3300
```

-continued

```
gaggccgacc agtgagcgga ggtggtgttg agcgtgaagc tcgagcgtcg accttggggg    3360
atttggcaag gtgttctcat tgaactagtc tttgggttta ttcgttgtta ttctaactcg    3420
cttctctacg gaatgactga gagttgtata ggatgaagta actttcttaa tatatgatat    3480
cacttgacag aggcatggtg tgcaaactgt gtgcattgtg gtagtggttt aggcctttca    3540
aacaggctgt cagttttatc gggggagatg aaggggggca ttgggagggc tgaaaagcat    3600
gctatgtctg gtaacatggt tatagtaaac gtgcattaca ttgaccaaga acgacaagaa    3660
ctaccagggt tgttacatca gtagcattaa gaacaagatg tgcattatgt cgaacacagc    3720
gacgtgatac tatgttcctt agcgattcga ccaaggtcta cggtcaggtg aggtcgatgg    3780
catcctcttc atcgtacgcc aacttcctgc gcttgctctg tgcgtgtgcc gaatcgtcta    3840
tgggcgccgg cttcgagccg acccgctcg cgcgactcgc ttcaggattt atgcgcggat    3900
agcaatcgca gacaggtgca gatggggagg taggctgagt ctaaggctga acgacgtttt    3960
agacgcgtca acttgacgtc cgcgtcaaac cacaaaacgc gtatgtacag ccgattcccg    4020
ccgcgcgctt gagaagttga gctcccgaaa acgccggaca acgctcaaat gtacggttcc    4080
tgcgctgcac cattcgtacc aggatcgtac gggagctaat atgcgggcgt gtaaaaattt    4140
tagatagaaa aatacataca agttgctgga cgacgaggat atgaaagcgt taagttcgaa    4200
gcatgccggg ctagattgga tcccgggtta tcgaagtatg gtcgcggcgc ggaagcgcca    4260
cccgcgaggc gcactggaag cacctgcata acgcctttgg gcaaatcgtg tgtttgctcg    4320
acgccgacag cggggaggaa cggcggtcct ccatggacta gagggcctcc ttcgcttgca    4380
ttagccacat ggcaggatga agagagaagg aatagacgcc taaccgcgcg accaacgcgc    4440
ctaaggcgcg cgcccttccg cgcactctcc ttccgcaacc gccaattgcc tacgcctcag    4500
ctacacaatc tgccccttgg tcgtgctgcc gcgttcatct tgctcgcttt gctaataaga    4560
acttgaacgt aacattcgca cttgggcccc gctgcaccca tgacgaaaag cccagcgcc    4620 tgggacgtta gcttcccaga tgaagccgcc gcaggtacat ccgcggcact cgcgccatcg    4680
caggctccgg acgcgtacc gcataatcct cccaggagaa gcgcgacatc cagaagtgaa    4740
tcccggaggg actctgaacc agtaagctgg tgtactttac ttatctgagt cgtaaactta    4800
ccccatacag gcgccaagc gtccgagagt cctgcagcct gaggatcgtc gcaagactct    4860
gccaggaccg agtaagcacg tttccttatg aaagaagcca gtcttatcat gtcgcctcca    4920
tacagagcgt gcgtacgtgc ccacgcccga agatatcaag gaggacgtca acacggtcgt    4980
cttcggcgaa gacgcggttg agcagtcggg cgcaagcgta gagaaaccca tccgcgcgct    5040
ttccgatttt gtagtgtttg acccgacgcg gggtttcgag cacatcatgc tcgacgtttt    5100
ggacaatgca acgcctggac gccatttcga ggccgccggc caagtaaggc ctatattctt    5160
gaatgaggaa gatgagggcc aggaagatgg cctggatgac ggagacggcg gcgaacaggc    5220
tcgtcaagta cagcgtataa gaacgagtgc gatattccgg tggtctctcg actatacgaa    5280
ggtcgacgag taagtggtcc tgggaaggtc ttcttccatc gtggcttacc ctttcttgac    5340
cagcccactc tatattgaaa cccaatatag ctggtttgag ttgcgcgcgc cggcccactc    5400
ctaccagcgc attcatcagc gtttctaccg tcctaaccgc atcgcgcaaa tcctcgtctc    5460
gacagcaatc aaatcaccag cgatgcccct cgacgagttt gcagaggcga actacgggga    5520
atgggacgct atgctcggcg aatatatttt cccagaagac atacaagaag ccgtatgtct    5580
gccctctggt caacgtattc tcgctcttat cttgtccaga tgcccttcgt tcggaccgtc    5640
attgacggat gtgaaccaga cgtgaggcgg cgggttctcg atgctcagtt tatcgccgac    5700
```

```
cttctgcgtc gtcaatccac cccgcacgtc cagacctccg ttccacggcc acgtgtaccg    5760
cccccgcaat acgtcaacct gacgagtctc acggggaatc tagatctcct cgtactgcaa    5820
ccggagaagc agaaccctac gcatgtttct gccttgatag acgtcctcgc tttgggactt    5880
tttcacgagc acctgaaggt ggtcggcccg ccgccaaagc acccgagcaa gcacaccctc    5940
aagctccagc aggccaagat gcgattggcc ttgacgagc tcgctaatcg ctgcatcgat    6000
gacaacacca cgatcagctt tccacacaat cgacgactgc gcgagaagta ttggagcgct    6060
gtcatagtgg acggcgtcac ttacgaggtg gcgttgtttg caggcttgta ttgctggccc    6120
acggccgctg atatacctct gtgatttaga taggcgactg cgttgttgtg caagcaaaca    6180
catatcggaa acgaccacct cgcaatctcc ccgacgacct gaccgaactt ccggcgaccg    6240
caatcgtcgc cgattacttc tggtacgttg taattttcgc ttgttactat cgcactcaac    6300
gctcttcgcc caggtttgcg aaggtcatat acatcgacca acacaagaag acgtccatg    6360 tccagtggta tgaacattcg tcgaaaacgt acttggatga gatctcggat ccgcacgagg    6420
tcttcttgtg gccaacgtgc gatgatattg acgccaggat cgttgtgggc aaggctacga    6480
ttcatcgcgc tcctccgact gataaggact ttggagctct ggaatacttc tgccggtgag    6540
ttgttctcct atttgcctcg tgctgactaa catttgctgc atgctcgata gctttgccta    6600
ccatgaggaa gatggttcgt tccaggacat cgacgacagg acgatttcac tgctgcagac    6660
tgtccacccc ccggaaaatt gtgctacatg tcatttccaa gagcaacaga ccgaggagtc    6720
gacttgcgtc gtggagggcg gcgccctgca ttatggtggg cacacatatc atgtggacga    6780
ctatgctctc tacgctgcct caggcggtgg accagcgtgt gtcggtagga tcacggagat    6840
ccattcgcct cggcccgctc gagcttcgac ttcccccaag gtccgtgtcg ctcgactagg    6900
ccggaggtcg gatgtcggct atttccccaa caagatggtc cacgaggtgt gcatcagtta    6960
tgctctgcat aaagtgtttg gtttgattga tattcatgca gcgggagctc ttcctgactg    7020
ggccaacaga gacagtagaa ctggatgcca aggcccttct gaagccatgt gtggtggtac    7080
acaagtccga tgtgcttgac ctggaggcct ggtttgacat ctcgccttc aacttctacg    7140 cccggtatcg gctccctacc ttgaacagcc cttgggcaca aagaaaata ctgcacagaa    7200 cagatgttct ggcttgtgat atctgtatag aacaacataa cgaacggttt cagcttctgt    7260
cagacctgag ctcaggtggt caggtttgtc tgcgcacttt cgaccctttc ggaggagtgg    7320
gggcctttgg actcgccatg gaagaactcg gctgcatgaa acttacacat gctgtggaga    7380
tcactcccag tgccgccttg acactaaggt atgtgttttt gtggagataa atctatggct    7440
aactctattg taggaaaaac tcaccagaga cagtggtatt caaccaatgt tccaacctgg    7500
tattccagta tgctgtcaag taccatgccg gaaacctcag cagcaatgat atggtgaagg    7560
atctttatga caacactcca attggcaagc ctccctgccc tggggatatt gactgcatag    7620
tagcaggttt cccttggtga gcccaaactc cttgatattt cttcattact gactatcact    7680
catagtcagc cccattccca gctcaacatg ttcaagaaag ccaacgatcg gaagacaaac    7740
ttgatactca accttctgtc ctgggtggac ttcttgcggc cgaagtattg tttcttcgag    7800
aacgtgcgcg gcttcttgag ctccactctc catgcaagac aagcgagcaa ataccgggtc    7860
gagggcggca tcaagatggg cggcttgaag ttccttaccc gttcactatt ggctatgggg    7920
tgagtgtctc acgcgcttat catacaggaa gcttgcatgc ctgcaggtcg actctagagg    7980
atcccc                                                              7986
```

<210> SEQ ID NO 2
<211> LENGTH: 5762
<212> TYPE: DNA
<213> ORGANISM: Trametes versicolor

<400> SEQUENCE: 2

```
tggagctcgc gcgcctgcag gtcgacacta gtggatctac ctcccgtgag aggaacgacg      60
gcgtcgggcc tttctcacgc gcagcgccga cttcgcgcga cagccgctgg tcagggcagc     120
acagacatct cccatcaccc agcttatacg ctcagttccg gcaccgagtc tgacgaatgc     180
ggcccgcctg caatcccgac actgctcggg gcgcgcgatc agactttccg tgaggacgta     240
aggtgctgtc ggccacctct cgacgctctc acgcataccg cagaattcgc gcgacgaccg     300
cgttccaggg cccttgacag atgctgacac cggtgcaatc ttgacactgt accaaccggg     360
taagtctcgt ccttggttct cggggactgg cgccggtcgc taccccttgg tcattcactc     420
taccagagcg ctggcttcgc cgaggtataa aggatgttgc gcgaaaccct caacacccca     480
actcaagccc cacttgagct tttgcgagat cctccacata ccactcacta ctttcaagtt     540
cttcaacatg tcgaggtttc actctcttct cgctttcgtc gttgcttccc ttgcggctgt     600
ggcccacgct ggtatcggtc ctgtcgccga cctcaccatc accaacgcag cggtcagccc     660
cgacggtttt tctcgccagg ccgtcgtcgt gaacggcggc accctggcc ctctcatcac      720
cggtaacatg gttcgtctcg gcgcgcacta gcggattgta tcgttcctga cacactgttg     780
caggggatc gcttccagct caatgtcatc gacaacctca cgaaccacac gatgctgaag       840
agcaccagta ttgtgagcta gtattcctcc tggaggaggc ttcattgtgc taataatcgt     900
cgtgtccagc actggcacgg tttcttccag aagggcacca actgggccga cggtcccgcc     960
ttcatcaacc agtgcccgat ctcatctggc cactcgttcc tgtatgactt ccaggttcct    1020
gaccaggctg taagtacgg tcgttatgga gtgtactgcg cattgctaaa tcgcatggtg     1080
aacaggcacc ttctggtacc acagtcactt gtccacgcag tactgtgatg gtctgagggg    1140
tccattcgtt gtttacgacc cgaatgaccc ggccgccgac ctgtacgacg tcgacaacgg    1200
taaggacgaa ttcgaaccgt aaatacccgc ttactgataa cttccgacg aattagacga     1260
cacggtcatt acccttgcgg attggtacca cgtcgccgcg aagctgggcc ccgcattccc    1320
gtaagtccat gggcattgtg ctattgaatc tctcttaact gtgcatatca gtctcggcgc    1380
cgacgccact ctcatcaacg gtaagggacg ctccccccagc acgaccaccg cggacctcac    1440
tgttatcagc gtcactccgg gtaaacggta tgctatatct tatcttatct gatggtactt    1500
tactgagaca tgctctagtt accgtttccg cctggtgtcc ctgtcgtgcg accccaacca    1560
caccttcagc atcgatggcc acaacatgac gatcatcgag accgactcga tcaacacggc    1620
gccctcgtg gtcgactcca ttcagatctt cgccgcccag cgttactcct tcgtggtaag     1680
tttgattcct ttcatgaggt tggtcgcaat tagtgattgt atggtcatgt agctcgaggc    1740
caaccaggcc gtcgacaact actggattcg cgccaacccg agcttcggta acgtcgggtt    1800
caccggcggc atcaactcgg ctatccttcg ctatgatggc gccgctgcca tcgagcccac    1860
caccacgcag accacttcga ccgagccgct caacgaggtc aacctgcacc cgctggttgc    1920
caccgctgtc gtatgtaata tcttccgtga ttgagcgcat cgttgctgac ttcgaccccc    1980
acagcctggc tctcccgttg cgggtggtgt tgacctggcc atcaatatgg cgttcaactt    2040
caatggcacc aacttcttca tcaacggcgc gtctttcacg ccccgaccg tgcctgtcct     2100
cctccagatc atcagcggcg cgcagaacgc gcaggacctc ctgccctccg gcagcgtata    2160
```

```
ctcgctcccc tcgaacgccg acatcgagat ctccttcccc gccaccgccg ctgccccgg     2220 tgcgccccac cccttccact tgcatgggca cgcgttcgcg gtcgtccgca gcgccggcag    2280
cacggtctac aactacgaca accccatctt ccgcgacgtc gtcagcacgg ggacgcctgc    2340
ggccggtgac aacgtcacca tccgcttccg caccgacaac cccggcccgt ggttcctcca    2400
ctgccacatc gacttccacc tcgaggccgg cttcgccgtc gtgttcgcgg aggacatccc    2460
cgacgtcgcg tcggcgaacc ccgtccccca ggcgtggtcc gacctctgcc cgacctacga    2520
cgcgctcgac cccagcgacc agtaaatggc ttgcgccggt cgatgatagg atatggacgg    2580
tgacttcgca cttgcaatac ggactctcgc ctcattatgg ttacacactc gctctggatc    2640
tctcgtctgt cgtcggaaca aatttgtata attcgcttaa tggttgaaac aaatggaata    2700
ttgggttatt atgcacgcat ttccctgttt gagcgatgga atgatccacg gttaaaaatg    2760
cgttagcgta acttcaagtc gaccatgctt agctgtagtg cacttgcggt acgaggtgtt    2820 acgcttttg cacgactcct tactactcaa ctatactcaa cgctatagct ctaggttgca     2880
ggcagttggc gttcaatatg atggaactaa tagctccata cattctggtt ggttgtacac    2940
tgcgtgttta ctaatcgcta caagatacat ccacttcacg aactgctatc tttgggccac    3000
gtcgcgatct tcaccgcgct ccccgtgagc gtgaacgtgt gcgtcagctt cgcgtccgtg    3060
tcgagcgcga gcgtgtacgt cccagggtgc acccacttct ccccatcctc atccgcgcgc    3120
gcgatcgcgc ccagcgtcac cggcagctgc gcgaccgtgc tcccccgcgg cgcgagccca    3180
tggatgcgcg tgtacgcgac gagcgtcttc ttcgggtgcg gcgcgggccc aaaggagcca    3240
ctcacgaaca gcagcgcgac gtagtcggac gcgaccttcc ccgtgttcgt cacgcgcacc    3300
gcgaacgtgt cgagggggcgc caggtccagg aacgccacgc tctcctggcc gtgcgtcacc    3360
agctgcgaga tggagtacga tttcgcgggg ccgccgaacg acgcggtgga gtcggcgcca    3420
ggggcggccc aggcgaacgc gaaggttgtg tagtgcagcc cgaagccgaa ctcgaagact    3480
ggggtgccgg agtaccactt gtacgtgcgc ccggggttcg tcgcgctcgg gcgcagagtc    3540
atatccgtca tcgggacctg ttcggcgtac gcggcagggt actgcgtgat gggtaggcgt    3600
cccgcggggg ccgccttgcc cgtgaggatg tcgaagagcg cggtgccgcc gctctggccg    3660
gggtagccgc cccagatgat tgcgtttacc tggtggagta gatgtgcacc cgcgtgatta    3720
gctcctgtcg cgggcgtagt tacaagcaaa agggaatgga atggtacgca ctgctttact    3780
gtgcttgagg gcggtgtcgt cgagctggcc gccaccaaac tgcgcgacga tcagcggctt    3840
gcctacgcgc tctagttccg cgacgaggtc gagttggttt cctggccagg ttacgttgag    3900
gcggtctatc tcctcgcgct cgaccgtttc gtcgagccct ccgcgaaga ccaccgcgtc     3960 cgcgcgcttc gcggcagcga cggcggctgc aaagccgctc gtgtcgttgc gggtagtcac    4020
gttggtgccg aatacatact ccacctcaaa tcctgcttgc tgggcacctt gtactgggct    4080
cacgaggtaa ggggcgatac cgaagtagtt gccctgcatg agccgcgtgg cgttcgccca    4140
ggggccgatg agcgcaagct tgcggacgcg tttcgacagc gggaggagcc cgtcgttctt    4200
cagcaggacc atgccctcga cggcagcggt atgtgcgagc tgctgagctt gcggagtgtt    4260
cacgtcaggc catcctagct gacggtaagg ttgtgccgct ggatcgtcga agtagccgag    4320
gctgcagagt tcgtttagaa tagatttcgg gcataacaga aggtcactta ccggacgagc    4380
gatgcgtatt ggcggatagc tgctctacgg aggtccgtcg agttgaccaa acccgttgc    4440 agcgcctcgg gaagataggt ggacgagaat gtcccacagt cgatgtcagt tcctgcgagc    4500
```

-continued

| | |
|---|---|
| agcgcgtccg ccgccgcttg cgccgggtcg gtggtatagt tgtgcggcgt gaaaatgttt | 4560 |
| tgcacagcgt cgcagtcgct cgtaacccac cgatcgtccg taaagcccca gtggtcgcgg | 4620 |
| agcacgtcct gcagcaggaa gctgttcgca cacgacggga tgccgttcac ggcgttgtac | 4680 |
| gagcacatca cgctcgcgac cttcgcgtcg cgcacgcacg tctggaacgg cgggaggtag | 4740 |
| aactcggaca ggtcctgctg cgagacgacc gcgttgaacc cgtagcgcac gacgccctcc | 4800 |
| cagttgtcca tgtcgtacgc ggcgaagtgc ttgcagtcgg cgacgacctt gaagtacggc | 4860 |
| ttcgggtcga gcccgccttg caggcccagg atgaggttgt agacatattg ggaaaggtgg | 4920 |
| aacggatcct ctcccggggt ctcctggccg cggccccatc ggggatcctt gaacgctatt | 4980 |
| agacgctgtt tggtgagcgg tcccacaacg gagagtagaa gagaagactc acggttgata | 5040 |
| ttgggcgtcc aataatcgag accagcgcgg ccgacgttgt tgaaggcacg ccattctgtg | 5100 |
| ctcacgatgg tcgcgatcgc ttgaatgagt gggtcatcga acgcggcacc catcagaatg | 5160 |
| gtttggggga aggaggtcgc ataactgaaa ttgccggatg gtgcaaaggt cacacccggg | 5220 |
| ctctggctta caccgtgcta aacataaaaa tgagtatatt gcgacataga taggccgaga | 5280 |
| tacgtaccaa accttctgac caccagttgt aggcgggaag acctagacgg ggtacacccg | 5340 |
| gagaggcgtt gactgtgttg ttagtgagct cctcgtcagt ccagatgcta atgagcgccg | 5400 |
| tagctcgagt gatagggtcc ttggtgacat cacagacggc gttgttcttc agcgggccgt | 5460 |
| tgacacaatc cgggaagcca tacgcccgaa cggtcgcagc gccgacggag aacgcggtga | 5520 |
| gaaacgcgtg gagacgacgc agaccgttcg ctatctagac aggcaggaac gtgaggagac | 5580 |
| agtccaccac gaaccgttcc attttgccct ctcttttaac ggggaactgg gcgttacgtg | 5640 |
| ccagggagaa cgtcggagct gggggcgaag agcatgatcc aaagaattca aaagcttct | 5700 |
| cgagagtact tctagagcgg ccgcgggccc atcgattttc cacccggtgg gtaccagtaa | 5760 |
| tt | 5762 |

<210> SEQ ID NO 3
<211> LENGTH: 2387
<212> TYPE: DNA
<213> ORGANISM: Trametes versicolor

<400> SEQUENCE: 3

| | |
|---|---|
| cagtatgtga agcctctggg gattcctgta gaatcatatg tgaggaaccg acgagcttcc | 60 |
| catgcttcca ccgcatatcg tgtagtctcc taccaagcag taaccctaac ggctctttcg | 120 |
| gtacaccgta cggagtgcga cggaaaggtc gcggacgtag tgagagaaac gatatgttca | 180 |
| caagacctat atcatgagaa caggaacgct agagtcgtcg gccgaaaaca agtcgggtat | 240 |
| ccgtgaggca gatatcacgt tgaccaggtt tgcgttggtg gcggatgttg cgacggtttg | 300 |
| tacgtaccgt acatggcgta caagacgcgg gagtgagccg tgcaaaatgg gacgaatagg | 360 |
| aaccccgtag ccgatatgga ccgcaccgga gggattgttg cccatacata agccatatgt | 420 |
| tctcgccgtg ccgcgccgag agctggtgtg cgcactagtg ggtgctatta gaagccgagc | 480 |
| gaggtaccgt ccctcaggcc aattggggaa taggacggag gcattcgagt aaaatacaca | 540 |
| tgggcatgcc tggatggagg catgcacatg cgcaggaggt tagtgcagcg cggccaatag | 600 |
| gagggcagga cggagtgaga tcaggagcga gtctggacgg gccgaagagt gagcgagagc | 660 |
| agaggcgcgg tgtggccgca cctgatgtta gagcaaagct tatttctgaa ctcgcggctc | 720 |
| gtggaggcca gacaggagta cgagcataga caggcgagag cggccggcga ggcgtcgagg | 780 |
| tcgggcggag atcacgtcca tccgtccatt ctgtctgcag cctgtgctta caggcaccgg | 840 |

-continued

```
gacagaggcg tacgatgacg tcgtatcgga cggaggagcg cacgaaacgg agcgcggatc    900
ttgatgtttg cgttagagag cagcgggatg agcgaggacg agcgttgaca aacgtctgac    960
tgagcagggc aagcaagagc tccgtgctgc gcggcggtgg gagggaagag ccgagggcgt   1020
gattggacga gggaaggagt catccagacc gcgtcttcgg cgaactgggc gaagaaggct   1080
ggaagagcga cgaggctcgc cggcgcgcgc gcacgctggg ctgctatcga ttgatggtcg   1140
ctcgagcagc gacgttggcc gaggcactgt cctcgaaaga ctcaaatcgt acggtgggcc   1200
ggacatggcc taccggcgac caatccgcga tgggcaaatg tcggtctcgt tatccacgca   1260
cgttctatct cgcccgttgg cacgcccaag gacgactgcg ctgcgactgg gcagtcgtcg   1320
tgggggaaaa cactgcgagg tgcgcggaag ggtgtcgaag gccaaggacg agcggagaac   1380
gggcggcggc gcgggccagc gagcgcccaa agcggaagga cagcacaggc gctgggcggg   1440
tagcgtccga tccatctcag ataagaatcg cccctgcggt atataacgca gaccttgcgc   1500
cccgactgaa ccccatcctc tcatcccatc caccacatcc acatgtcggt cagtacccgg   1560
ctcacccttg cagtccctgc atgcgctgac ctctccctgc agcaacaagt caacgtcgga   1620
atcaacgggt aagatcgctc gcggacttga attcaccgca tacatcctaa tctcgcccaa   1680
tccgcgtcct tttccagttt cggtgagcct gctccctccc tcgcttttaa tcgcgcgcat   1740
atactcaccc attcgcaggt cgtatcggcc gtatcgtcct ccgtaatgcc ctccagcacg   1800
gcaagatcaa tgtcgtcgct gtgaacgagt aagcgcgccc aatctgcatc gcgtaaatca   1860
gacgcgctct aactccctgc gcgcagccct ttcatcgacc ttgagtacat ggtctacatg   1920
ttcaagtacg actccgtcca cggccgcttc aagggcacg tcgaggtcaa ggacggcaag    1980
ctctgggtcg agggcaagcc catcaccgtc ttccaggaga aggacgccgc caacattccc   2040
tggggctccg ccggcgccga ctacatcgtc gagtccaccg tgtcttcac caccaccgaa    2100 aagtgcgcat acactcaccc aaacatggca ttttgtgact gacgcggttc ccgatcgata   2160
gggcctctgc ccacttgaag gcggtgcca agaaggtcat catctccgcc ccctccgccg    2220
acgcgcccat gttcgtctgc ggtgttaacc tggactcgta cgaccccaag tacactgtcg   2280
tgcgtgcatt ttcccatcgc gtcgcgcgag aaccccgatt tacctccgcc cgcgtgtaga   2340
tccactagtg tcgacctgca ggcgcgcgag ctccagcttt tgttccc                 2387
```

```
<210> SEQ ID NO 4
<211> LENGTH: 21
<212> TYPE: DNA
<213> ORGANISM: Artificial sequence
<220> FEATURE:
<221> NAME/KEY: primer_bind
<222> LOCATION: (1)..(21)
<223> OTHER INFORMATION: Description of artificial sequence: cDNA

<400> SEQUENCE: 4
tccagctcga ccttgcgccg c                                               21

<210> SEQ ID NO 5
<211> LENGTH: 21
<212> TYPE: DNA
<213> ORGANISM: Artificial sequence
<220> FEATURE:
<221> NAME/KEY: primer_bind
<222> LOCATION: (1)..(17)
<223> OTHER INFORMATION: Description of artificial sequence: cDNA

<400> SEQUENCE: 5
```
ggatccgacg tggaggagcc g                                              21

<210> SEQ ID NO 6
<211> LENGTH: 17
<212> TYPE: DNA
<213> ORGANISM: Artificial sequence
<220> FEATURE:
<221> NAME/KEY: primer_bind
<222> LOCATION: (1)..(17)
<223> OTHER INFORMATION: Description of artificial sequence: cDNA
<221> NAME/KEY: primer_bind
<222> LOCATION: (9)..(9)
<223> OTHER INFORMATION: "n" has the meaning "a or g or c or t/u"

<400> SEQUENCE: 6
tggcayggnt tyttyca                                                   17

<210> SEQ ID NO 7
<211> LENGTH: 14
<212> TYPE: DNA
<213> ORGANISM: Artificial sequence
<220> FEATURE:
<221> NAME/KEY: primer_bind
<222> LOCATION: (1)..(14)
<223> OTHER INFORMATION: Description of artificial sequence: cDNA

<400> SEQUENCE: 7
tcdatrtgrc artg                                                      14

<210> SEQ ID NO 8
<211> LENGTH: 27
<212> TYPE: DNA
<213> ORGANISM: Artificial sequence
<220> FEATURE:
<221> NAME/KEY: primer_bind
<222> LOCATION: (1)..(27)
<223> OTHER INFORMATION: Description of artificial sequence: cDNA
<221> NAME/KEY: primer_bind
<222> LOCATION: (24)..(24)
<223> OTHER INFORMATION: "n" has the meaning "a or g or c or t/u"

<400> SEQUENCE: 8
attcagggat cctggtayca ywsncay                                        27

<210> SEQ ID NO 9
<211> LENGTH: 27
<212> TYPE: DNA
<213> ORGANISM: Artificial sequence
<220> FEATURE:
<221> NAME/KEY: primer_bind
<222> LOCATION: (1)..(27)
<223> OTHER INFORMATION: Description of artifical sequence: cDNA
<221> NAME/KEY: primer_bind
<222> LOCATION: (16)..(16)
<223> OTHER INFORMATION: "n" has the meaning "a or g or c or t/u"
<221> NAME/KEY: primer_bind
<222> LOCATION: (22)..(22)
<223> OTHER INFORMATION: "n" has the meaning "a or g or c or t/u"

<400> SEQUENCE: 9
atacgaggat ccrtgnccrt gnarrtg                                        27

<210> SEQ ID NO 10
<211> LENGTH: 23
<212> TYPE: DNA
<213> ORGANISM: Artificial sequence
<220> FEATURE:
<221> NAME/KEY: primer_bind
<222> LOCATION: (1)..(23)
<223> OTHER INFORMATION: Description of artificial sequence: cDNA

```
<400> SEQUENCE: 10
cgtatcggcc gtatcgtcct ccg                                              23

<210> SEQ ID NO 11
<211> LENGTH: 23
<212> TYPE: DNA
<213> ORGANISM: Artificial sequence
<220> FEATURE:
<221> NAME/KEY: primer_bind
<222> LOCATION: (1)..(23)
<223> OTHER INFORMATION: Description of artificial sequence: cDNA

<400> SEQUENCE: 11
cgcccttcaa gtgggcagag gcc                                              23

<210> SEQ ID NO 12
<211> LENGTH: 13
<212> TYPE: DNA
<213> ORGANISM: Artificial sequence
<220> FEATURE:
<221> NAME/KEY: misc_feature
<223> OTHER INFORMATION: Description of artificial sequence: adaptor
      cDNA, forward strand

<400> SEQUENCE: 12
aattcgcggc cgc                                                         13

<210> SEQ ID NO 13
<211> LENGTH: 13
<212> TYPE: DNA
<213> ORGANISM: Artificial sequence
<220> FEATURE:
<221> NAME/KEY: misc_feature
<222> LOCATION: (1)..(13)
<223> OTHER INFORMATION: Description of artificial sequence: adaptor
      cDNA, backward strand

<400> SEQUENCE: 13
aattgcggcc gcg                                                         13
```